US011400109B2

(12) United States Patent
Karve et al.

(10) Patent No.: US 11,400,109 B2
(45) Date of Patent: Aug. 2, 2022

(54) SUBCUTANEOUS DELIVERY OF MESSENGER RNA

(71) Applicant: Translate Bio, Inc., Lexington, MA (US)

(72) Inventors: Shrirang Karve, Lexington, MA (US); Frank DeRosa, Lexington, MA (US); Zarna Bhavsar, Lexington, MA (US); Michael Heartlein, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 16/349,229

(22) PCT Filed: Nov. 10, 2017

(86) PCT No.: PCT/US2017/061176
§ 371 (c)(1),
(2) Date: May 10, 2019

(87) PCT Pub. No.: WO2018/089846
PCT Pub. Date: May 17, 2018

(65) Prior Publication Data
US 2019/0298755 A1    Oct. 3, 2019

Related U.S. Application Data

(60) Provisional application No. 62/420,435, filed on Nov. 10, 2016.

(51) Int. Cl.
| | | |
|---|---|---|
| *A61K 31/7105* | (2006.01) | |
| *A61K 47/69* | (2017.01) | |
| *A61K 38/47* | (2006.01) | |
| *C12N 9/26* | (2006.01) | |
| *A61P 3/00* | (2006.01) | |
| *A61K 9/00* | (2006.01) | |
| *A61K 9/127* | (2006.01) | |
| *A61K 38/45* | (2006.01) | |

(52) U.S. Cl.
CPC ........ *A61K 31/7105* (2013.01); *A61K 9/0019* (2013.01); *A61K 9/1271* (2013.01); *A61K 38/45* (2013.01); *A61K 38/47* (2013.01); *A61K 47/6925* (2017.08); *A61P 3/00* (2018.01); *C12N 9/2474* (2013.01); *C12Y 201/03003* (2013.01); *C12Y 302/01035* (2013.01)

(58) Field of Classification Search
None
See application file for complete search history.

(56) References Cited

U.S. PATENT DOCUMENTS

| | | | |
|---|---|---|---|
| 2011/0076273 A1* | 3/2011 | Adler .................... | A61K 45/06 424/133.1 |
| 2013/0236974 A1* | 9/2013 | de Fougerolles .... | A61K 9/1272 435/455 |
| 2019/0275170 A1* | 9/2019 | Benenato ............... | A61P 35/02 |

FOREIGN PATENT DOCUMENTS

| | | |
|---|---|---|
| WO | 2011/068810 A1 | 6/2011 |
| WO | WO 2013/151666 A2 | 10/2013 |
| WO | 2015/138348 A1 | 9/2015 |

OTHER PUBLICATIONS

Pardi et al. J Control Release 217, 345-351 (Year: 2015).*
Geary et al. Advanced Drug Delivery Reviews 87 46-51 (Year: 2015).*
Frost et al. Expert Opinion on Drug Delivery 4:4 427-440 (Year: 2007).*
International Report on Patentability for International Patent Application No. PCT/US2017/061176, dated May 14, 2019 (10 pages).
International Search Report and Written Opinion for International Patent Application No. PCT/US2017/061176, dated May 3, 2018 (19 pages).

* cited by examiner

*Primary Examiner* — Brian Whiteman
(74) *Attorney, Agent, or Firm* — Proskauer Rose LLP; Fangli Chen

(57) ABSTRACT

The present invention provides, among other things, methods of formulating nucleic acid-containing nanoparticles with an enzyme to afford efficient delivery of payload to a cell or tissue of interest via subcutaneous administration. In some embodiments, the present invention provides a process in which mRNA-loaded lipid nanoparticles are co-mixed with various amounts of hyaluronidase and administered via subcutaneous administration. The resulting payload can be efficiently delivered to the liver and other organs or tissues of a treated subject.

17 Claims, 10 Drawing Sheets

Specification includes a Sequence Listing.

```
SEQUENCE LISTING

<160> NUMBER OF SEQ ID NOS: 8

<210> SEQ ID NO 1
<211> LENGTH: 140
<212> TYPE: RNA
<213> ORGANISM: Artificial Sequence
<220> FEATURE:
<223> OTHER INFORMATION: chemically synthesized oligonucleotide

<400> SEQUENCE: 1
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg                                                  140

<210> SEQ ID NO 2
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 2
cggguggcau cccugugacc ccuccccagu gccucuccug gcccuggaag uugccacucc      60
agugcccacc agccuugucc uaauaaaauu aaguugcauc aagcu                     105

<210> SEQ ID NO 3
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 3 gggguggcauc ccugugaccc cuccccagug ccucuccugg cccuggaagu ugccacucca     60
gugcccacca gccuuguccu aauaaaauua aguugcauca aagcu                     105

<210> SEQ ID NO 4
<211> LENGTH: 1310
<212> TYPE: RNA
<213> ORGANISM: Artificial Sequence
<220> FEATURE:
<223> OTHER INFORMATION: chemically synthesized oligonucleotide

<400> SEQUENCE: 4
```

| | |
|---|---:|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcuguuca accuucggau cuugcugaac aacgcugcgu | 180 |
| uccggaaugg ucacaacuuc augguccgga acuucagaug cggccagccg cuccagaaca | 240 |
| aggugcagcu caaggggagg gaccuccuca cccugaaaaa cuucaccgga gaagagauca | 300 |
| aguacaugcu guggcuguca gccgaccuca aauuccggau caagcagaag ggcgaauacc | 360 |
| uuccuuugcu gcagggaaag ucccugggga ugaucuucga gaagcgcagc acucgcacua | 420 |
| gacugucaac ugaaaccggc uucgcgcugc ugggaggaca ccccugcuuc cugaccaccc | 480 |
| aagauaucca ucugggugug aacgaauccc ucaccgacac agcgcgggug cugucgucca | 540 |
| uggcagacgc gguccucgcc cgcguguaca agcagucuga ucuggacacu cuggccaagg | 600 |
| aagccuccau uccuaucauu aauggauugu ccgaccucua ccaucccauc cagauucugg | 660 |
| ccgauuaucu gacucugcaa gaacauuaca gcucccugaa ggggcuuacc cuuucgugga | 720 |
| ucggcgacgg caacaacauu cugcacagca uuaugaugag cgcugccaag uuuggaaugc | 780 |
| accuccaagc agcgaccccg aagggauacg agccagacgc cuccgugacg aagcuggcug | 840 |
| agcaguacgc caaggagaac ggcacuaagc ugcugcucac caacgacccu cucgaagccg | 900 |
| cccacgugg caacgugcug aucaccgaua ccuggaucuc cauggacag gaggaggaaa | 960 |
| agaagaagcg ccugcaagca uuucagggu accaggugac uaugaaaacc gccaaggucg | 1020 |
| ccgcccucgga cuggaccuuc uugcacaguc ugcccagaaa gcccgaagag guggacgacg | 1080 |
| agguguucua cagcccgcgg ucgcuggucu uccggaggc cgaaaacagg aaguggacua | 1140 |
| ucauggccgu gaugguguc cugcugaccg auuacuccc gcagcugcag aaaccaaagu | 1200 |
| ucugacgggu ggcaucccug ugaccccucc ccagugccuc uccuggcccu ggaaguugcc | 1260 |
| acuccagugc ccaccagccu uguccuaaua aaauuaaguu gcaucaagcu | 1310 |

<210> SEQ ID NO 5
<211> LENGTH: 1310
<212> TYPE: RNA
<213> ORGANISM: Artificial Sequence
<220> FEATURE:
<223> OTHER INFORMATION: chemically synthesized oligonucleotide

<400> SEQUENCE: 5

| | |
|---|---:|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcuguuca accuucggau cuugcugaac aacgcugcgu | 180 |
| uccggaaugg ucacaacuuc augguccgga acuucagaug cggccagccg cuccagaaca | 240 |
| aggugcagcu caaggggagg gaccuccuca cccugaaaaa cuucaccgga gaagagauca | 300 |
| aguacaugcu guggcuguca gccgaccuca aauuccggau caagcagaag ggcgaauacc | 360 |
| uuccuuugcu gcagggaaag ucccugggga ugaucuucga gaagcgcagc acucgcacua | 420 |
| gacugucaac ugaaaccggc uucgcgcugc ugggaggaca ccccugcuuc cugaccaccc | 480 |
| aagauaucca ucugggugug aacgaauccc ucaccgacac agcgcgggug cugucgucca | 540 |
| uggcagacgc gguccucgcc cgcguguaca agcagucuga ucuggacacu cuggccaagg | 600 |
| aagccuccau uccuaucauu aauggauugu ccgaccucua ccaucccauc cagauucugg | 660 |
| ccgauuaucu gacucugcaa gaacauuaca gcucccugaa ggggcuuacc cuuucgugga | 720 |

| | |
|---|---|
| ucggcgacgg caacaacauu cugcacagca uuaugaugag cgcugccaag uuuggaaugc | 780 |
| accuccaagc agcgacaccg aagggauacg agccagacgc cuccgugacg aagcuggcug | 840 |
| agcaguacgc caaggagaac ggcacuaagc ugcugcucac caacgacccu cucgaagccg | 900 |
| cccacgugg caacgugcug aucaccgaua ccuggaucuc cauggacag gaggaggaaa | 960 |
| agaagaagcg ccugcaagca uuucaggggu accaggugac uaugaaaacc gccaaggucg | 1020 |
| ccgccucgga cuggaccuuc uugcacaguc ugcccagaaa gcccgaagag guggacgacg | 1080 |
| agguguucua cagcccgcgg ucgcuggucu uccggaggc cgaaaacagg aaguggacua | 1140 |
| ucauggccgu gaugguguc cugcugaccg auuacucccc gcagcugcag aaaccaaagu | 1200 |
| ucugagggug gcaucccugu gaccccuccc cagugccucu ccuggcccug gaaguugcca | 1260 |
| cuccagugcc caccagccuu guccuaauaa aauuaaguug caucaaagcu | 1310 |

<210> SEQ ID NO 6
<211> LENGTH: 1310
<212> TYPE: RNA
<213> ORGANISM: Artificial Sequence
<220> FEATURE:
<223> OTHER INFORMATION: chemically synthesized oligonucleotide

<400> SEQUENCE: 6

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg augcuguuua accgagaau ucugcugaac aacgccgcgu | 180 |
| ucaggaacgc ccacaauuuc augguccgca acuuuagaug cggacagccu ucccaaaaca | 240 |
| agguccagcu caaggggcgg gacuugcuga cccuuaagaa cuuuaccggc gaagagauca | 300 |
| aguacaugcu gugguugca gcggaccuga aguccgcau caagcagaaa gggagauauc | 360 |
| ugccgcugcu ccaaggaaag ucgcucggca ugaucuucga gaagcgucg accagaaccc | 420 |
| ggcuguccac ugaaacuggu uucgcccuuc uggguggaca cccuuguuuc cugacaaccc | 480 |
| aggacaucca ucugggcgug aacgaaagcc ucacugacac cgccagggug cugagcucca | 540 |
| uggccgacgc uguccuugcc cggguguaca agcaguccga ucuggacacu cuggccaagg | 600 |
| aagcguccau cccgaucauu aacggacugu ccgaccugua ccacccgauc cagauucugg | 660 |
| ccgacuaccu gaccuugcaa gagcacuaca gcucacugaa gggcuugacc cugagcugga | 720 |
| ucggcgacgg aaacaacauu cugcauucga ucaugaguc cgcggccaag uucggaaugc | 780 |
| aucugcaggc cgcaacuccc aagggauacg aaccugaugc guccgugacu aagcuggccg | 840 |
| agcaguacgc aaaggaaaac ggcaccaagc ugcugcugac caacgacccg cucgaagcug | 900 |
| cccacgagg gaacgugcuc auuaccgaca cuuggaucuc caugggcag gaagaagaga | 960 |
| agaagaagcg gcuccaggca uuccagggu accaggucac caugaaaacg gccaaagugg | 1020 |
| ccgcuucgga uuggacuuuc ucccacugcc uucccgcaa accugaggaa guggaugaug | 1080 |
| aaguguucua cucccacgc ucccgcgugu ucccgaggc cgagaaucgg aaguggacca | 1140 |
| uuauggccgu gaugguguca cugcugaccg acuacagccc caacugcaa agccgaagu | 1200 |
| ucugacgggu ggcaucccug ugaccccucc cagugccuc ccuggcccu ggaaguugcc | 1260 |
| acuccagugc ccaccagccu uguccuaaua aaauuaaguu gcaucaagcu | 1310 |

<210> SEQ ID NO 7
<211> LENGTH: 1239
<212> TYPE: RNA
<213> ORGANISM: Artificial Sequence
<220> FEATURE:
<223> OTHER INFORMATION: chemically synthesized oligonucleotide

<400> SEQUENCE: 7

```
augagcagca agggcagcgu ggugcuggcc uacagcggcg gccuggacac cagcugcauc      60
cugguguggc ugaaggagca gggcuacgac gugaucgccu accuggccaa caucggccag     120
aaggaggacu ucgaggaggc ccgcaagaag gcccugaagc ugggcgccaa gaaggucuuc     180
aucgaggacu ugaccgcga guucguggag gaguucaucu ggcccgccau ccagagcagc     240
gcccuguacg aggaccgcua ccugcuggc accagccugg cccgccccug caucgcccgc     300
aagcaggugg agaucgccca cgcgagggc gccaaguacg ugagccacgg cgccaccggc     360
aagggcaacg accaggugcg cuucgagcug agcugcuaca ccuggcccc ccagaucaag     420
gugaucgccc ccuggcgcau gcccgaguuc uacaaccgcu ucaagggccg caacgaccug     480
auggaguacg ccaagcagca cggcauccc auccccguga ccccaagaa cccucuggagc     540
auggacgaga accugaugca caucagcuac gaggccggca uccuggagaa ccccaagaac     600
caggccccc ccggccugua caccaagacc caggaccccg ccaaggcccc caacacccc      660
gacauccugg agaucgaguu caagaagggc gugccccguga aggugaccaa cgugaaggac     720
ggcaccaccc accagaccag ccuggagcug uucaguuacc ugaacgaggu ggccggcaag     780
cacggcgugg gccgcaucga caucguggag aaccgcuuca ucggcaugaa gagccgcggc     840
aucuacgaga ccccgccgg caccauccug uaccacgcc accuggacau cgaggccuuc     900
accauggacc gcgaggugcg caagaucaag cagggccugg gccugaaguu cgccgagcug     960
gguguacaccg gcuucuggca cagccccgag ugcgaguucg ugcgccacug caucgccaag    1020
agccaggagc gcguggaggg caaggugcag gugagcgugc ugaagggcca ggguacauc     1080
cuggggccgcg agagcccccu gagccuguac aacgaggagc uggugagcau gaacgugcag    1140
ggcgacuacg agcccaccga cgccaccggc uucaucaaca ucaacagccu gcgccugaag    1200
gaguaccacc gccugcagag caaggugacc gccaaguga                          1239
```

<210> SEQ ID NO 8
<211> LENGTH: 1359
<212> TYPE: RNA
<213> ORGANISM: Artificial Sequence
<220> FEATURE:
<223> OTHER INFORMATION: chemically synthesized oligonucleotide

<400> SEQUENCE: 8

```
augagcaccg ccgugcugga aaccccggc cugggccgca agcugagcga cuucggccag      60
gagaccagcu acaucgagga caacugcaac cagaacggcg ccaucagccu gaucuucagc    120
cugaaggagg aggugggcgc ccuggccaag gugcugcgcc uguucgagga gaacgacgug    180
aaccugaccc acaucgagag ccgccccagc cgccugaaga aggacgagua cgaguucuuc    240
acccaccugg acaagcgcag ccugcccgcc cugaccaaca ucaucaagau ccugcgccac    300
gacauccggcg ccaccgugca cgagcugagc cgcgacaaga gaaggacac cgugcccugg    360
uuccccccgca ccauccagga gcuggaccgc uucgccaacc agauccugag cuacggcgcc    420
gagcuggacg ccgaccaccc cggcuucaag accccgugu accgcgcccg ccgcaagcag    480
uucgccgaca ucgccuacaa cuaccgccac ggccagccca uccccgcgu ggaguacaug    540
gaggaggaga gaagaccug gggcaccgug uucaagaccc ugaagagccu guacaagacc    600
cacgccugcu acgaguacaa ccacaucuuc ccccugcugg agaaguacug cggcuuccac    660
```

-continued

| | |
|---|---|
| gaggacaaca ucccccagcu ggaggacgug agccaguucc ugcagaccug caccggcuuc | 720 |
| cgccugcgcc ccguggccgg ccugcugagc agccgcgacu uccugggcgg ccuggccuuc | 780 |
| cgcguguucc acugcaccca guacauccgc cacggcagca agcccaugua cacccccgag | 840 |
| cccgacaucu gccacgagcu gcugggccac gugccccugu ucagcgaccg cagcuucgcc | 900 |
| caguucagcc aggagaucgg ccuggccagc cugggcgccc ccgacgagua caucgagaag | 960 |
| cuggccacca ucuacugguu caccguggag uucggccugu gcaagcaggg cgacagcauc | 1020 |
| aaggccuacg gcgccggccu gcugagcagc uucggcgagc ugcaguacug ccugagcgag | 1080 |
| aagcccaagc ugcugccccu ggagcuggag aagaccgcca uccagaacua caccgugacc | 1140 |
| gaguuccagc cccuguacua cguggccgag agcuucaacg acgccaagga gaaggugcgc | 1200 |
| aacuucgccg ccaccauccc ccgccccuuc agcgugcgcu acgaccccua cacccagcgc | 1260 |
| aucgaggugc uggacaacac ccagcagcug aagauccugg ccgacagcau caacagcgag | 1320 |
| aucggcaucc ugugcagcgc ccugcagaag aucaaguaa | 1359 |

SUBCUTANEOUS DELIVERY OF MESSENGER RNA

RELATED APPLICATIONS

This application is a 35 U.S.C. § 371 National Stage Application of International Application No. PCT/US17/61176, filed Nov. 10, 2017, which claims priority to U.S. Provisional Application Ser. No. 62/420,435, filed Nov. 10, 2016, the disclosure of which is hereby incorporated by reference.

SEQUENCE LISTING

The present specification makes reference to a Sequence Listing (submitted electronically as a .txt file named "MRT-1251US1 Sequence Listing ST25" on May 10, 2019). The .txt file was generated May 10, 2019 and is 10,469 bytes in size. The entire contents of the Sequence Listing are herein incorporated by reference.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to deliver mRNA for efficient in vivo delivery of mRNA.

While intravenous or infusion method is commonly used to deliver the mRNA encapsulated in lipid nanoparticles to the patient in need of treatment, such method may not be preferred by patients because of the prolonged time and the additional medical attention needed for the administration. More patient-friendly delivery methods are needed.

SUMMARY OF INVENTION

The present invention provides, among other things, improved methods and compositions for the effective in vivo delivery of mRNA via subcutaneous administration. In particular, mRNA is injected subcutaneously with an enzyme capable of degrading extracellular matrices such as a hyaluronidase for efficient exposure to the circulation. As described herein, mRNA when co-injected subcutaneously with hyaluronidase resulted in unexpectedly efficient delivery of mRNA and protein expression in vivo, particularly in the liver. Although hyaluronidase had been used to enhance subcutaneous delivery of small molecule and protein drugs, it was uncertain prior to the present invention if hyaluronidase could also be effective in facilitating subcutaneous delivery of mRNA in particular mRNA encapsulated in lipid nanoparticles (LNPs), in view of the significant size differences and the complexity of the LNP-mRNA formulations. Typical proteins including antibodies have an average size below 20 nm. Many mRNA-loaded LNPs have sizes close to or around about 100 nM, which is at least five times as large as a typical protein. Therefore, the highly efficient delivery of mRNA, protein production, protein activity and therapeutic efficacy demonstrated in multiple disease models observed by the present inventors were truly, surprising and represents a significant improvement in the field of mRNA delivery. In view of efficient mRNA delivery and high protein expression in the liver, the present invention is particularly useful in treating metabolic diseases such as ornithine transcarbamylase (OTC) deficiency, among other things. In addition, the hyaluronidase based subcutaneous delivery of mRNA provided in the present application is more patient friendly, can reduce healthcare costs and increase patient throughput at the hospital.

In one aspect, the present disclosure provides a method of treating ornithine transcarbamylase (OTC deficiency) by mRNA therapy. The method comprises administering to a subject in need of treatment via subcutaneous route a composition for subcutaneous delivery comprising messenger RNA encoding OTC protein and a hyaluronidase enzyme.

In some embodiments, the hyaluronidase enzyme is administered at a dose of 50,000 Units (U) or less. In some embodiments, the hyaluronidase enzyme is administered at a dose amount of less than 40,000 U, less than 30,000 U, less than 20,000 U, less than 10,000 U, less than 9000 U, less than 8000 U, less than 7000 U, less than 6000 U, less than 5000 U less than 4000 U, less than 3000 U, less than 2000 U, less than 1000 U, less than 900 U, less than 800 U, less than 700 U, less than 600 U, or less than 500 U.

In some embodiments, the hyaluronidase enzyme is administered at a dose of 1 U or more. In some embodiments, the hyaluronidase enzyme is administered at a dose of at least 5 U, at least 10 U, at least 20 U, at least 30 U, at least 40 U, at least 50 U, at least 60 U, at least 70 U, at least 80 U, at least 100 U, or at least 150 U.

In some embodiments, the hyaluronidase enzyme is administered at a dose amount of at least 160 U, at least 180 U, at least 200 U, at least 220 U, at least 240 U, at least 260 U, at least 280 U, at least 300 U, at least 320 U, at least 340 U, at least 360 U, at least 380 U, or at least 400 U. In some embodiments, the hyaluronidase enzyme is administered at a dose range of 1-50,000 U (e.g., 50-50,000 U, 50-45,000 U, 100-40,000 U, 100-35,000 U, 100-30,000 U, 150-30,000 U, 160-30,000 U, 160-25,000 U, 200-50,000 U, 200-40,000 U, 200-30,000 U, 250-30,000 U, 250-25,000 U, or 250-20,000 U).

In some embodiments, the hyaluronidase enzyme is administered at a dose amount of at least 1 U per mg of RNA delivered. In some embodiments, hyaluronidase is administered at a dose amount of at least 2 U per mg of RNA, at least 5 U per mg of RNA, at least 10 U per mg of RNA, at least 20 U per mg mRNA, at least 30 U per mg mRNA, at least 40 U per mg mRNA, at least 50 U per mg mRNA, at least 100 U per mg mRNA, at least 200 U per mg mRNA, at least 300 U per mg mRNA, at least 400 U per mg mRNA, at least 500 U per mg mRNA, at least 1000 U per mg RNA, at least 2000 U per mg of RNA, at least 3000 U per mg of RNA, at least 4000 U per mg of RNA, or at least 5000 U per mg of RNA.

In some embodiments, the mRNA has a length of or greater than about 0.5 kb, 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, or 15 kb.

In some embodiments, the mRNA is encapsulated within a nanoparticle. In some embodiments, the nanoparticle is a lipid-based or polymer-based nanoparticle. In some embodiments, the lipid-based nanoparticle is a liposome. In some embodiments, the liposome comprises a PEGylated lipid. In some embodiments, the PEGylated lipid constitutes at least 1%, at least 2%, at least 3%, at least 4%, at least 5%, at least 6%, at least 7%, at least 8%, at least 9%, or at least 10% of the total lipids in the liposome. In some embodiments, the PEGylated lipid constitutes at least 5% of the total lipids in the liposome. In some embodiments, the PEGylated lipid constitutes about 5% of the total lipids in the liposome. In some embodiments, the PEGylated lipid constitutes 10% or less, 9% or less, 8% or less, 7% or less, 6% or less, 5% or less, 4% or less, or 3% or less of the total lipids in the liposome. In some embodiments, the PEGylated lipid constitutes 5% or less of the total lipids in the liposome.

In some embodiments, the lipid nanoparticle comprises one or more cationic lipids. In some embodiments, the one or more cationic lipids are selected from the group consisting of C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLin-DAP, DLincarbDAP, DLinCDAP, KLin-K-DMA, DLin-K-XTC2-DMA, HGT4003, and combinations thereof.

In some embodiments, the lipid nanoparticle comprises one or more non-cationic lipids. In some embodiments, the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)) and combinations thereof.

In some embodiments, the subcutaneous injection results in expression of the OTC protein in the liver of the subject.

In some embodiments, the subcutaneous injection delivers mRNA to hepatocytes. In some embodiments, the subcutaneous injection results in OTC expression in hepatocytes.

In some embodiments, the subcutaneous injection results in expression of the OTC protein in the serum of the subject.

In some embodiments, the expression of the protein encoded by the mRNA is detectable at least 24 hours, 2 days, 3 days, 4 days, 5 days, 6 days, 1 week, 2 weeks, 3 weeks, 4 weeks, or 1 month post-administration.

In some embodiments, OTC expression after mRNA administration can be detected by a functional assay.

In some embodiments, the administering of the composition results in an increased OTC protein expression or activity level in serum of the subject as compared to a control level. In some embodiments, the control level is a baseline serum OTC protein expression or activity level in the subject prior to the treatment. In some embodiments, the control level is a reference level indicative of the average serum OTC protein expression or activity level in OTC patients without treatment.

In some embodiments, the administering of the composition results in a reduced urinary orotic acid level in the subject as compared to a control orotic acid level. In some embodiments, the control orotic acid level is a baseline urinary orotic acid level in the subject prior to the treatment. In some embodiments, the control orotic acid level is a reference level indicative of the average urinary orotic acid level in OTC patients without treatment.

In some embodiments, wherein the administering of the composition results in an increased citrulline level in serum of the subject as compared to a control citrulline level. In some embodiments, the control citrulline level is a baseline serum citrulline level in the subject prior to the treatment. In some embodiments, the control citrulline level is a reference level indicative of the average serum citrulline level in OTC patients without treatment.

In some embodiments, the mRNA encoding the OTC protein and the hyaluronidase enzyme are injected simultaneously.

In some embodiments, the mRNA encoding the OTC protein and the hyaluronidase enzyme are injected in one composition.

In some embodiments, the mRNA encoding the OTC protein and the hyaluronidase enzyme are injected in separate compositions.

In some embodiments, the mRNA encoding the OTC protein and the hyaluronidase enzyme are injected sequentially.

In some embodiments, the mRNA encoding the OTC protein and the hyaluronidase enzyme are injected in a volume of less than 20 ml, less than 15 ml, less than 10 ml, less than 5 ml, less than 4 ml, less than 3 ml, less than 2 ml, or less than 1 ml.

In some embodiments, the subcutaneous injection is performed once a week or less frequently. In some embodiments, the subcutaneous injection is performed twice a month or less frequently. In some embodiments, the subcutaneous injection is performed once a month or less frequently.

In another aspect, the present invention provides for a composition for treating ornithine transcarbamylase (OTC) deficiency), comprising an mRNA encoding an ornithine transcarbamylase (OTC) protein, and a hyaluronidase enzyme.

In some embodiments, the composition for treating OTC deficiency comprises the mRNA and/or the hyaluronidase enzyme, wherein, the mRNA and/or the hyaluronidase enzyme are encapsulated within a nanoparticle.

In certain embodiments, the mRNA and the hyaluronidase enzyme are encapsulated within the same nanoparticle.

In certain embodiments, the mRNA and the hyaluronidase enzyme are encapsulated in separate nanoparticles.

In certain embodiments, the separate nanoparticles encapsulating the mRNA and the hyaluronidase enzyme comprise the same formulation.

In certain embodiments, the separate nanoparticles encapsulating the mRNA and the hyaluronidase enzyme comprise the same formulation.

In some embodiments, the mRNA is encapsulated within the nanoparticle and the hyaluronidase enzyme is not encapsulated.

In some embodiments, the nanoparticle is a lipid-based or polymer-based nanoparticle.

In some embodiments, the lipid-based nanoparticle is a liposome.

In some embodiments the liposome comprises a PEGylated lipid. In some embodiments the PEGylated lipid constitutes at least 1%, at least 2%, at least 3%, at least 4%, at least 5%, at least 6%, at least 7%, at least 8%, at least 9%, or at least 10% of the total lipids in the liposome. In some embodiments, the PEGylated lipid constitutes at least 5% of the total lipids in the liposome. In some embodiments, the PEGylated lipid constitutes about 5% of the total lipids in the liposome.

In some embodiments, the mRNA comprises unmodified nucleotides. In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 4'thiouridine, 4'-thiocytidine, and/or 2-thiocytidine.

In some embodiments, the composition is in liquid form.

In some embodiments, the composition is lyophilized powder.

In one aspect, the present invention provides a method of messenger RNA (mRNA) delivery for in vivo protein expression, comprising, administering via subcutaneous injection to a subject an mRNA encoding a protein, and a hyaluronidase enzyme, wherein the subcutaneous injection results in in vivo expression of the protein encoded by the mRNA in the subject.

In some embodiments, the hyaluronidase enzyme is administered at a dose amount of less than 50,000 U, less than 40,000 U, less than 30,000 U, less than 20,000 U, less than 10,000 U, less than 9000 U, less than 8000 U, less than 7000 U, less than 6000 U, less than 5000 U less than 4000 U, less than 3000 U, less than 2000 U, less than 1000 U, less than 900 U, less than 800 U, less than 700 U, less than 600 U, or less than 500 U.

In some embodiments, the hyaluronidase enzyme is administered at a dose amount of at least 1 U, at least 5 U, at least 10 U, at least 20 U, at least 30 U, at least 40 U, at least 50 U, at least 60 U, at least 70 U, at least 80 U, at least 100 U, or at least 150 U.

In some embodiments, the hyaluronidase enzyme is administered at a dose amount of at least 160 U, at least 180 U, at least 200 U, at least 220 U, at least 240 U, at least 260 U, at least 280 U, at least 300 U, at least 320 U, at least 340 U, at least 360 U, at least 380 U, or at least 400 U. In other words, the hyaluronidase enzyme is administered at a dose range of 1-50,000 U.

In some embodiments, the hyaluronidase enzyme is administered at a dose amount of at least 10 U per mg mRNA, at least 20 U per mg mRNA, at least 30 U per mg mRNA, at least 40 U per mg mRNA, at least 50 U per mg mRNA, at least 100 U per mg mRNA, at least 200 U per mg mRNA, at least 300 U per mg mRNA, at least 400 U per mg mRNA, or at least 500 U per mg mRNA.

In some embodiments, the mRNA is encapsulated within a nanoparticle.

In some embodiments, the nanoparticle is a lipid-based or polymer-based nanoparticle.

In some embodiments, the lipid-based nanoparticle is a liposome.

In certain embodiments, the liposome comprises a PEGylated lipid.

In some embodiments, the PEGylated lipid constitutes 10% or less, 9% or less, 8% or less, 7% or less, 6% or less, 5% or less, 4% or less, or 3% or less of the total lipids in the liposome. In certain embodiments, the PEGylated lipid constitutes 5% or less of the total lipids in the liposome.

In certain embodiments, the method of subcutaneous injection results in expression of the protein in the liver of the subject.

In certain embodiments, the method of subcutaneous injection results in expression of the protein in the serum of the subject.

In some embodiments, the protein is detectable after at least 24 hours, 2 days, 3 days, 4 days, 5 days, 6 days, 1 week, 2 weeks, 3 weeks, 4 weeks, or 1 month post-injection. In some embodiments, the protein is detected by a functional assay.

In some embodiments, the mRNA and the hyaluronidase enzyme are injected simultaneously.

In some embodiments, the mRNA and the hyaluronidase enzyme are injected in one formulation.

In one or more embodiments, the mRNA and the hyaluronidase enzyme are injected in separate formulations.

In some embodiments, the mRNA and the hyaluronidase enzyme are injected sequentially.

In some embodiments, the mRNA and the hyaluronidase enzyme are injected in less than 20 ml, less than 15 ml, less than 10 ml, less than 5 ml, less than 4 ml, less than 3 ml, less than 2 ml, or less than 1 ml.

In one aspect, the invention provides a composition for delivery of mRNA for in vivo protein expression, comprising a) an mRNA encoding a protein, and b) a hyaluronidase enzyme.

In some embodiments, the mRNA and the hyaluronidase enzyme are encapsulated in a nanoparticle.

In some embodiments, the mRNA is encapsulated within a first nanoparticle and wherein the hyaluronidase enzyme is encapsulated within a second nanoparticle.

In some embodiments, the mRNA and the hyaluronidase enzyme are encapsulated in the same nanoparticle.

In some embodiments, the mRNA and the hyaluronidase enzyme are encapsulated in the separate nanoparticles.

In some embodiments, the mRNA is encapsulated within the nanoparticle and the hyaluronidase enzyme is not encapsulated.

In some embodiments, the nanoparticle is a lipid-based or polymer-based nanoparticle.

In some embodiments, the lipid-based nanoparticle is a liposome.

In some embodiments, the liposome comprises a PEGylated lipid.

In some embodiments, the PEGylated lipid constitutes at least 1%, at least 2%, at least 3%, at least 4%, at least 5%, at least 6%, at least 7%, at least 8%, at least 9%, or at least 10% of the total lipids in the liposome.

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the mRNA is unmodified.

In some embodiments, the composition is a liquid form.

In another embodiment the composition is a lyophilized powder.

In one aspect, the invention provides a container containing a composition described above. The container is a vial or a syringe. The syringe may be prefilled for single subcutaneous administration. The vial may contain lyophilized powder or liquid form of the composition.

An aspect of the invention provides a method of treating a disease, disorder or condition comprising delivering messenger RNA (mRNA) to a subject in need of treatment according to the methods described above, wherein the mRNA encodes a protein deficient in the subject.

In some embodiments the method and compositions described herein are useful in treating metabolic disorder. In some embodiments, the disease, disorder or condition is selected from ornithine transcarbamylase (OTC) deficiency, Phenylalanine hydroxylase (PAH) deficiency (phenylketonuria, PKU), argininosuccinate synthase 1 (ASS1) deficiency, erythropoietin (EPO) deficiency, Fabry disease; hemophilic diseases (such as, e.g., hemophilia B (FIX), hemophilia A (FVIII); SMN1-related spinal muscular atrophy (SMA); amyotrophic lateral sclerosis (ALS); GALT-related galactosemia; COL4A5-related disorders including Alport syndrome; galactocerebrosidase deficiencies; X-linked adrenoleukodystrophy; Friedreich's ataxia; Pelizaeus-Merzbacher disease; TSC1 and TSC2-related tuberous sclerosis; Sanfilippo B syndrome (MPS IIIB); the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only and not for limitation.

DEFINITIONS

Figure 1:
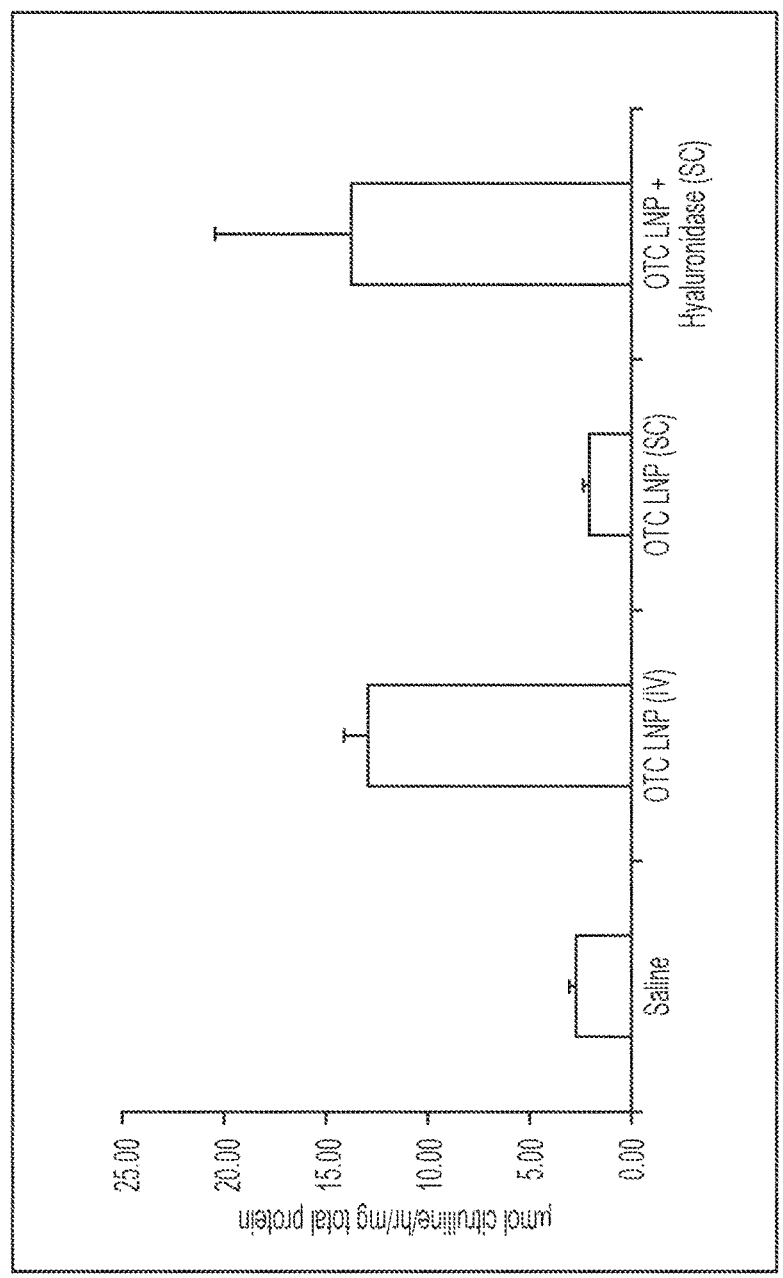
FIG. 1 depicts an exemplary comparison of citrulline activity of human ornithine transcarbamylase (hOTC) protein in the livers of OTC Knockout (KO) spf$^{ash}$ mice 24 hours after either intravenous administration or subcutaneous administration of a lipid nanoparticle (LNP) mRNA formulation with and without hyaluronidase.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Encapsulation: As used herein, the term "encapsulation," or grammatical equivalent, refers to the process of confining an individual mRNA molecule within a nanoparticle.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Half-life: As used herein, the term "half-life" is the time required for a quantity such as nucleic acid or protein concentration or activity to fall to half of its value as measured at the beginning of a time period.

Hyaluronidase: As used herein, the term "hyaluronidase" refers to the family of enzymes that are capable of degrading hyaluronic acid (hyaluronan).

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subcutaneous administration: As used herein, the term "subcutaneous administration" or "subcutaneous injection" refers to a bolus injection into the subcutis which is the tissue layer between the skin and the muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, improved methods and compositions of mRNA delivery by subcutaneous injection with a hyaluronidase enzyme. Unexpectedly, co-injection with an hyaluronidase enzyme resulted in surprisingly efficient systemic exposure and dispersion of the mRNA-loaded lipid nanoparticles. The resulting payload were efficiently delivered to the livers (and other organs or tissues) of treated animals. Such a hyaluronidase based method has major benefits to creating new delivery profiles of otherwise intolerable drugs. Several examples are presented herein which demonstrate efficient mRNA deposition, protein production, protein activity and efficacy in multiple disease models.

Among other things, the present invention provides methods and compositions for the treatment of ornithine transcarbamylase (OTC) deficiency by administering via subcutaneous injection to a subject in need of treatment an mRNA encoding an ornithine transcarbamylase (OTC) protein and a hyaluronidase enzyme. The invention may also be used to treat various other diseases, disorders and conditions in particular metabolic diseases, disorders and conditions.

Various aspects of the invention are described in detail in the following sections. The use of sections is not meant to limit the invention. Each section can apply to any aspect of the invention. In this application, the use of "or" means "and/or" unless stated otherwise.

Hyaluronidase Enzymes

Various hyluronidase enzymes may be used to practice the present invention. For example, there are three groups of hyluronidases based on their mechanisms of action. Two of the groups are endo-β-N-acetyl-hexosaminidases. One group includes the vertebrate enzymes that utilize substrate hydrolysis. The vertebrate hyaluronidases (EC 3.2.1.35) are endo-β-N-acetyl-hexosaminidases employing substrate hydrolysis for catalysis. The vertebrate hyaluronans also have transglycosidase activities, with the ability to cross-link chains of HA and the potential ability to cross-link chains of HA with ChS or Ch. The vertebrate hyaluronidases degrade HA through a non-processive endolytic process, generating mostly tetrasaccharides. Mammalian hyaluronidases are members of the group of carbohydrate-active enzymes (CAZy), termed glycosidase family 56, defined as endo-β-acetyl-hexosaminidases that utilize hydrolysis in catalysis of HA at the β1,4 glycosidic linkages.

The second group, which is predominantly bacterial, includes the eliminases that function by β-elimination of the glycosidic linkage with introduction of an unsaturated bond. Bacterial hyaluronidases are also endo-β-acetyl-hexosaminidases, but utilize the lyase mechanism. They belong to a different CAZy family, to polysaccharide lyase family 8. In general, these polysaccharide lyases (EC 4.2.2.*) cleave by β-elimination, resulting in a double bond at the new non-reducing end. The hyaluronate lyases (EC 4.2.2.1; bacterial Hyal) consists of only one subgroup within family 8 that also include: chondroitin ABC lyases (EC 4.2.2.4), chondroitin AC lyases (EC 4.2.2.5), and xanthan lyases (EC 4.2.2.12). All of these bacterial enzymes, hyaluronidases, chondroitinases, and xanthanases, share significant sequence, structural, and mechanistic homology.

The third group is the endo-β-glucuronidases. These are found in leeches, which are annelids, and in certain crustaceans.

In addition, there are six known genes coding for hyaluronidase-like sequences in human genome, Hyal-1, Hyal-2, Hyal-3, Hyal-4, and PH-20/Spam1 and a pseudogene Phyal1 (not translated), all of which have high degree of homology. Mice also have six genes coding for hyaluronidases which have high degree of homology with human genes (Stern et al., Chem. Rev. 2006, 106(3): 818-839). In some embodiments, hyaluronidase may also be obtained from cows or pigs as a sterile preparation which is free of any other animal substance.

Bovine PH-20 is a commonly used hyaluronidase, and is available commercially in a reasonably pure form (Sigma catalog no. H3631, Type VI-S, from bovine testes, with an activity of 3,000 to 15,000 national formulary units (NFU) units/mg).

Hyaluronidase for injection can be obtained commercially in powder form or in solution. For example, an FDA approved bovine testicular hyaluronidase enzyme is available as a colorless orderless solution.

In some embodiments, an International Unit for hyaluronidase may be defined as the activity of 0.1 mg of the International Standard Preparation, and is equal to one turbidity reducing unit (TRU) (Humphrey J H et al., "International Standard for Hyaluronidase," Bull World Health Organ. 1957; 16(2): 291-294) based on the following reaction:

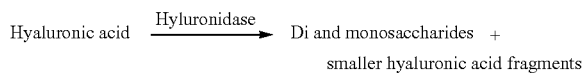

Accordingly, one unit of Hyaluronidase activity will cause a change in $A_{600}$ of 0.330 per minute at pH 5.3 at 37° C. in a 2.0 ml reaction mixture (45 minute assay). % Transmittance is determined at 600 nm, Light path=1 cm.

In some embodiments, a recombinant enzyme, or an artificially produced enzyme by any known or available standard methods may be used for the present purpose.

In some embodiments, a hyaluronidase is used, at a dose amount ranging between 1-50,000 Units for subcutaneous injection. An exemplary recombinant hyaluronidase of this type is the endoglycosidase Hylenex. The administered subcutaneous dose of hyaluronidase is about 1 Unit to 50,000 Units. The hyaluronidase is administered at a dose amount of less than 40,000 U, less than 30,000 U, less than 20,000 U, less than 10,000 U, less than 9000 U, less than 8000 U, less than 7000 U, less than 6000 U, less than 5000 U less than 4000 U, less than 3000 U, less than 2000 U, less than 1000 U, less than 900 U, less than 800 U, less than 700 U, less than 600 U, or less than 500 U. In some embodiments, the hyaluronidase enzyme is administered at a dose amount of at least 1 U, at least 5 U, at least 10 U, at least 20 U, at least 30 U, at least 40 U, at least 50 U, at least 60 U, at least 70 U, at least 80 U, at least 100 U, or at least 150 U. In some other embodiments, the hyaluronidase enzyme is administered at a dose amount of at least 160 U, at least 180 U, at least 200 U, at least 220 U, at least 240 U, at least 260 U, at least 280 U, at least 300 U, at least 320 U, at least 340 U, at least 360 U, at least 380 U, or at least 400 U. In one or more embodiments, a porcine (pig) hyaluronidase is used at a dose ranging between 1-50,000 Units. The hyaluronidase enzyme is administered at a dose amount of less than 40,000 U, less than 30,000 U, less than 20,000 U, less than 10,000 U, less than 9000 U, less than 8000 U, less than 7000 U, less than 6000 U, less than 5000 U less than 4000 U, less than 3000 U, less than 2000 U, less than 1000 U, less than 900 U, less than 800 U, less than 700 U, less than 600 U, or less than 500 U. The method of any one of the preceding claims, wherein the hyaluronidase enzyme is administered at a dose amount of at least 1 U, at least 5 U, at least 10 U, at least 20 U, at least 30 U, at least 40 U, at least 50 U, at least 60 U, at least 70 U, at least 80 U, at least 100 U, or at least 150 U. In some other embodiments, the hyaluronidase enzyme is administered at a dose amount of at least 160 U, at least 180 U, at least 200 U, at least 220 U, at least 240 U, at least 260 U, at least 280 U, at least 300 U, at least 320 U, at least 340 U, at least 360 U, at least 380 U, or at least 400 U.

In one or more embodiments, hyaluronidase is administered simultaneously with the mRNA. In some embodiments, hyaluronidase may be administered prior to the administration of the mRNA. In some embodiments, the mRNA and the hyaluronidase enzyme are part of the same formulation. In some embodiments, the RNA and the hyaluronidase enzyme are injected as separate formulations.

In some embodiments, the hyaluronidase enzyme may be administered in an aqueous solution. In some embodiments, the enzyme is administered in saline solution. In some embodiments the hyaluronidase enzyme is part of the mRNA formulation and is present in the same solution, the solution comprising mRNA-encapsulated lipid nanoparticles. In some embodiments a lyophilized preparation comprising the mRNA-encapsulated lipid and the hyaluronidase enzyme is formulated for therapeutic use.

Messenger RNA (mRNA)

The present invention may be used to deliver any mRNA. As used herein, mRNA is the type of RNA that carries information from DNA to the ribosome for translation of the encoded protein. mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to deliver mRNAs of a variety of lengths. In some embodiments, the present invention may be used to deliver in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to deliver mRNA that is unmodified or mRNA containing one or more modifications that typically enhance stability. In some embodiments, modifications are selected from modified nucleotides, modified sugar phosphate backbones, and 5' and/or 3' untranslated region (UTR).

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' inverted triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' inverted triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of $m^7$GpppG, $m^7$GpppA, $m^7$GpppC; unmethylated cap analogs (e.g., GpppG); dimethylated cap analog (e.g., $m^{2,7}$GpppG), trimethylated cap analog (e.g., $m^{2,2,7}$GpppG), dimethylated symmetrical cap analogs (e.g., $m^7$Gpppm$^7$G), or anti reverse cap analogs (e.g. ARCA; $m^{7,2'Ome}$GpppG, $m^{72'd}$GpppG, $m^{7,3'Ome}$GpppG, $m^{7,3'd}$GpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m⁷G") linked via a triphosphate bridge to the 5'-end of the first transcribed nucleotide, resulting in m⁷G (5')ppp(5')N, where N is any nucleoside. A preferred embodiment of a m⁷G cap utilized in embodiments of the invention is m⁷G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m⁷G cap analogs are known in the art, many of which are commercially available. These include the m⁷GpppG described above, as well as the ARCA 3'-OCH₃ and 2'-OCH₃ cap analogs (Jemiclity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

While mRNA provided from in vitro transcription reactions may be desirable in some embodiments, other sources of mRNA are contemplated as within the scope of the invention including mRNA produced from bacteria, fungi, plants, and/or animals.

The present invention may be used to deliver mRNAs encoding a variety of proteins. Non-limiting examples of mRNAs suitable for the present invention include mRNAs encoding target proteins such as argininosuccinate synthetase (ASS1), firefly luciferase (FFL), phenylalanine hydroxylase (PAH), and Ornithine transcarbamylase (OTC).

Exemplary mRNA Sequences

In some embodiments, the present invention provides methods and compositions for delivering mRNA encoding a target protein to a subject for the treatment of the target protein deficiency. Exemplary mRNA sequences are shown below.

Construct Design:
X—mRNA coding sequence—Y

5' and 3' UTR Sequences
X (5' UTR Sequence) =
(SEQ ID NO: 1)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACG Y (3' UTR Sequence) =
(SEQ ID NO: 2)
CGGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAUC
AAGCU
OR
(SEQ ID NO: 3)
GGGUGGCAUCCCUGUGACCCCUCCCCAGUGCCUCUCCUGGAAGU
UGCCACUCCAGUGCCCACCAGCCUUGUCCUAAUAAAAUUAAGUUGCAUCA
AGCU An Exemplary Full-Length Codon-Optimized Human Ornithine Transcarbamylase (OTC) Messenger RNA Sequence is Shown Below:

(SEQ ID NO: 4)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCUGUUCA

ACCUUCGGAUCUUGCUGAACAACGCUGCGUUCCGGAAUGGUCACAACUUC

AUGGUCCGGAACUUCAGAUGCGGCCAGCCGCUCCAGAACAAGGUGCAGCU

CAAGGGGAGGGACCUCCUCACCCUGAAAAACUUCACCGGAGAAGAGAUCA

AGUACAUGCUGUGGCUGUCAGCCGACCUCAAAUUCCGGAUCAAGCAGAAG

GGCGAAUACCUUCCUUUGCUGCAGGGAAAGUCCCUGGGGAUGAUCUUCGA

GAAGCGCAGCACUCGCACUAGACUGUCAACUGAAACCGGCUUCGCGCUGC

UGGGAGGACACCCCUGCUUCCUGACCACCCAAGAUAUCCAUCUGGGUGUG

AACGAAUCCCUCACCGACACAGCGCGGGUGCUGUCGUCCAUGGCAGACGC

GGUCCUCGCCCGCGUGUACAAGCAGUCUGAUCUGGACACUCUGGCCAAGG

AAGCCUCCAUUCCUAUCAUUAAUGGAUUGUCCGACCUCUACCAUCCCAUC

CAGAUUCUGGCCGAUUAUCUGACUCUGCAAGAACAUUACAGCUCCCUGAA

GGGGCUUACCCUUUCGUGGAUCGGCGACGGCAACAACAUUCUGCACAGCA

UUAUGAUGAGCGCUGCCAAGUUUGGAAUGCACCUCCAAGCAGCGACCCCG

AAGGGAUACGAGCCAGACGCCUCCGUGACGAAGCUGGCUGAGCAGUACGC

CAAGGAGAACGGCACUAAGCUGCUGCUCACCAACGACCCUCUCGAAGCCG

CCCACGGUGGCAACGUGCUGAUCACCGAUACCUGGAUCUCCAUGGGACAG

GAGGAGGAAAAGAAGAAGCGCCUGCAAGCAUUUCAGGGGUACCAGGUGAC

UAUGAAAACCGCCAAGGUCGCCGCCUCGGACUGGACCUUCUUGCACUGUC

UGCCCAGAAAGCCCGAAGAGGUGGACGACGAGGUGUUCUACAGCCCGCGG

UCGCUGGUCUUUCCGGAGGCCGAAAACAGGAAGUGGACUAUCAUGGCCGU

GAUGGUGUCCCUGCUGACCGAUUACUCCCCGCAGCUGCAGAAACCAAAGU

UCUGACGGGUGGCAUCCCUGUGACCCCUCCCCAGUGCCUCUCCUGGCCCU

GGAAGUUGCCACUCCAGUGCCCACCAGCCUUGUCCUAAUAAAAUUAAGUU

GCAUCAAGCU.

In Exemplary Full Length Codon-Optimized Human Ornithine Transcarbamylase (OTC) Messenger RNA Sequence is Shown Below:

(SEQ ID NO: 5)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCUGUUCA

ACCUUCGGAUCUUGCUGAACAACGCUGCGUUCCGGAAUGGUCACAACUUC

AUGGUCCGGAACUUCAGAUGCGGCCAGCCGCUCCAGAACAAGGUGCAGCU

CAAGGGGAGGGACCUCCUCACCCUGAAAAACUUCACCGGAGAAGAGAUCA

AGUACAUGCUGUGGCUGUCAGCCGACCUCAAAUUCCGGAUCAAGCAGAAG

GGCGAAUACCUUCCUUUGCUGCAGGGAAAGUCCCUGGGGAUGAUCUUCGA

GAAGCGCAGCACUCGCACUAGACUGUCAACUGAAACCGGCUUCGCGCUGC

UGGGAGGACACCCCUGCUUCCUGACCACCCAAGAUAUCCAUCUGGGUGUG

AACGAAUCCCUCACCGACACAGCGCGGGUGCUGUCGUCCAUGGCAGACGC

GGUCCUCGCCCGCGUGUACAAGCAGUCUGAUCUGGACACUCUGGCCAAGG

AAGCCUCCAUUCCUAUCAUUAAUGGAUUGUCCGACCUCUACCAUCCCAUC

CAGAUUCUGGCCGAUUAUCUGACUCUGCAAGAACAUUACAGCUCCCUGAA

GGGGCUUACCCUUUCGUGGAUCGGCGACGGCAACAACAUUCUGCACAGCA

UUAUGAUGAGCGCUGCCAAGUUUGGAAUGCACCUCCAAGCAGCGACCCCG

AAGGGAUACGAGCCAGACGCCUCCGUGACGAAGCUGGCUGAGCAGUACGC

CAAGGAGAACGGCACUAAGCUGCUGCUCACCAACGACCCUCUCGAAGCCG

CCCACGGUGGCAACGUGCUGAUCACCGAUACCUGGAUCUCCAUGGGACAG

GAGGAGGAAAAGAAGAAGCGCCUGCAAGCAUUUCAGGGGUACCAGGUGAC

UAUGAAAACCGCCAAGGUCGCCGCCUCGGACUGGACCUUCUUGCACUGUC

UGCCCAGAAAGCCCGAAGAGGUGGACGACGAGGUGUUCUACAGCCCGCGG

UCGCUGGUCUUUCCGGAGGCCGAAAACAGGAAGUGGACUAUCAUGGCCGU

GAUGGUGUCCCUGCUGACCGAUUACUCCCCGCAGCUGCAGAAACCAAAGU

UCUGAGGGUGGCAUCCCUGUGACCCCUCCCCAGUGCCUCUCCUGGCCCUG

GAAGUUGCCACUCCAGUGCCCACCAGCCUUGUCCUAAUAAAAUUAAGUUG

CAUCAAGCU.

Another Exemplary Full Length Codon-Optimized Human Ornithine Transcarbamylase (OTC) Messenger RNA Sequence is Shown Below:

(SEQ ID NO: 6)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACGAUGCUGUUUA
ACCUGAGAAUUCUGCUGAACAACGCCGCGUUCAGGAACGGCCACAAUUUC
AUGGUCCGCAACUUUAGAUGCGGACAGCCUCUCCAAAACAAGGUCCAGCU
CAAGGGGCGGGACUUGCUGACCCUUAAGAACUUUACCGGCGAAGAGAUCA
AGUACAUGCUGUGGUUGUCAGCGGACCUGAAGUUCCGCAUCAAGCAGAAA
GGGGAGUAUCUGCCGCUGCUCCAAGGAAAGUCGCUCGGCAUGAUCUUCGA
GAAGCGCUCGACCAGAACCCGGCUGUCCACUGAAACUGGUUUCGCCCUUC
UGGGUGGACACCCUUGUUUCCUGACAACCCAGGACAUCCAUCUGGGCGUG
AACGAAAGCCUCACUGACACCGCCAGGGUGCUGAGCUCCAUGGCCGACGC
UGUCCUUGCCCGGGUGUACAAGCAGUCCGAUCUGGACACUCUGGCCAAGG
AAGCGUCCAUCCCGAUCAUUAACGGACUGUCCGACCUGUACCACCCGAUC
CAGAUUCUGGCCGACUACCUGACCUUGCAAGAGCACUACAGCUCACUGAA
GGGCUUGACCCUGAGCUGGAUCGGCGACGGAAACAACAUUCUGCAUUCGA
UCAUGAUGUCCGCGGCCAAGUUCGGAAUGCAUCUGCAGGCCGCAACUCCC
AAGGGAUACGAACCUGAUGCGUCCGUGACUAAGCUGGCCGAGCAGUACGC
AAAGGAAAACGGCACCAAGCUGCUGCUGACCAACGACCCGCUCGAAGCUG
CCCACGGAGGGAACGUGCUCAUUACCGACACUUGGAUCUCCAUGGGGCAG
GAAGAAGAGAAGAAGAAGCGGCUCCAGGCAUUCCAGGGUUACCAGGUCAC
CAUGAAAACGGCCAAAGUGGCCGCUUCGAUUGGACUUUCCUCCACUGCC
UUCCCCGCAAACCUGAGGAAGUGGAUGAUGAAGUGUUCUACUCCCCACGC
UCCCUCGUGUUCCCCGAGGCCGAGAAUCGGAAGUGGACCAUUAUGGCCGU
GAUGGUGUCACUGCUGACCGACUACAGCCCCCAACUGCAAAAGCCGAAGU
UCUGACGGUGGCAUCCCUGUGACCCCUCCCCAGUGCCUCUCCUGGCCCU
GGAAGUUGCCACUCCAGUGCCCACCAGCCUUGUCCUAAUAAAAUUAAGUU
GCAUCAAGCU

Exemplary Codon-Optimized Human ASS1 (CO-hASS1) Coding Sequence (SEQ ID NO: 7)
AUGAGCAGCAAGGGCAGCGUGGUGCUGGCCUACAGCGGCGGCCUGGACAC
CAGCUGCAUCCUGGUGUGGCUGAAGGAGCAGGGCUACGACGUGAUCGCCU
ACCUGGCCAACAUCGGCCAGAAGGAGGACUUCGAGGAGGCCCGCAAGAAG
GCCCUGAAGCUGGGCGCCAAGAAGGUGUUCAUCGAGGACGUGAGCCGCGA
GUUCGUGGAGGAGUUCAUCUGGCCCGCCAUCCAGAGCAGCGCCCUGUACG
AGGACCGCUACCUGCUGGGCACCAGCCUGGCCCGCCCCUGCAUCGCCCGC
AAGCAGGUGGAGAUCGCCCAGCGCGAGGGCGCCAAGUACGUGAGCCACGG
CGCCACCGGCAAGGGCAACGACCAGGUGCGCUUCGAGCUGAGCUGCUACA
GCCUGGCCCCCCAGAUCAAGGUGAUCGCCCCCUGGCGCAUGCCCGAGUUC
UACAACCGCUUCAAGGGCCGCAACGACCUGAUGGAGUACGCCAAGCAGCA
CGGCAUCCCCAUCCCCGUGACCCCCAAGAACCCCUGGAGCAUGGACGAGA
ACCUGAUGCACAUCAGCUACGAGGCCGGCAUCCUGGAGAACCCCAAGAAC
CAGGCCCCCCCGGCCUGUACACCAAGACCCAGGACCCCGCCAAGGCCCC
CAACACCCCCGACAUCCUGGAGAUCGAGUUCAAGAAGGGCGUGCCCGUGA
AGGUGACCAACGUGAAGGACGGCACCACCCACCAGACCAGCCUGGAGCUG
UUCAUGUACCUGAACGAGGUGGCCGGCAAGCACGGCGUGGGCCGCAUCGA
CAUCGUGGAGAACCGCUUCAUCGGCAUGAAGAGCCGCGGCAUCUACGAGA
CCCCCGCCGGCACCAUCCUGUACCACGCCCACCUGGACAUCGAGGCCUUC
ACCAUGGACCGCGAGGUGCGCAAGAUCAAGCAGGGCCUGGGCCUGAAGUU
CGCCGAGCUGGUGUACACCGGCUUCUGGCACAGCCCCGAGUGCGAGUUCG
UGCGCCACUGCAUCGCCAAGAGCCAGGAGCGCGUGGAGGGCAAGGUGCAG
GUGAGCGUGCUGAAGGGCCAGGUGUACAUCCUGGGCCGCGAGAGCCCCCU
GAGCCUGUACAACGAGGAGCUGGUGAGCAUGAACGUGCAGGGCGACUACG
AGCCCACCGACGCCACCGGCUUCAUCAACAUCAACAGCCUGCGCCUGAAG
GAGUACCACCGCCUGCAGAGCAAGGUGACCGCCAAGUGA Exemplary Codon-Optimized Human PAH (CO-hPAH) Coding Sequence (SEQ ID NO: 8)
AUGAGCACCGCCGUGCUGGAGAACCCCGGCCUGGGCCGCAAGCUGAGCGA
CUUCGGCCAGGAGACCAGCUACAUCGAGGACAACUGCAACCAGAACGGCG
CCAUCAGCCUGAUCUUCAGCCUGAAGGAGGAGGUGGGCGCCCUGGCCAAG
GUGCUGCGCCUGUUCGAGGAGAACGACGUGAACCUGACCCACAUCGAGAG
CCGCCCCAGCCGCCUGAAGAAGGACGAGUACGAGUUCUUCACCCACCUGG
ACAAGCGCAGCCUGCCCGCCCUGACCAACAUCAUCAAGAUCCUGCGCCAC
GACAUCGGCGCCACCGUGCACGAGCUGAGCCGCGACAAGAAGAAGGACAC
CGUGCCCUGGUUCCCCCGCACCAUCCAGGAGCUGGACCGCUUCGCCAACC
AGAUCCUGAGCUACGGCGCCGAGCUGGACGCCGACCACCCCGGCUUCAAG
GACCCCGUGUACCGCGCCCGCCGCAAGCAGUUCGCCGACAUCGCCUACAA
CUACCGCCACGGCCAGCCCAUCCCCCGCGUGGAGUACAUGGAGGAGGAGA
AGAAGACCUGGGGCACCGUGUUCAAGACCCUGAAGAGCCUGUACAAGACC
CACGCCUGCUACGAGUACAACCACAUCUUCCCCCUGCUGGAGAAGUACUG
CGGCUUCCACGAGGACAACAUCCCCCAGCUGGAGGACGUGAGCCAGUUCC
UGCAGACCUGCACCGGCUUCCGCCUGCGCCCCGUGGCCGGCCUGCUGAGC
AGCCGCGACUUCCUGGGCGGCCUGGCCUUCCGCGUGUUCCACUGCACCCA
GUACAUCCGCCACGGCAGCAAGCCCAUGUACACCCCCGAGCCCGACAUCU
GCCACGAGCUGCUGGGCCACGUGCCCCUGUUCAGCGACCGCAGCUUCGCC
CAGUUCAGCCAGGAGAUCGGCCUGGCCAGCCUGGGCGCCCCCGACGAGUA
CAUCGAGAAGCUGGCCACCAUCUACUGGUUCACCGUGGAGUUCGGCCUGU

```
                                   -continued
GCAAGCAGGGCGACAGCAUCAAGGCCUACGGCGCCGGCCUGCUGAGCAGC

UUCGGCGAGCUGCAGUACUGCCUGAGCGAGAAGCCCAAGCUGCUGCCCCU

GGAGCUGGAGAAGACCGCCAUCCAGAACUACACCGUGACCGAGUUCCAGC

CCCUGUACUACGUGGCCGAGAGCUUCAACGACGCCAAGGAGAAGGUGCGC

AACUUCGCCGCCACCAUCCCCCGCCCCUUCAGCGUGCGCUACGACCCCUA

CACCCAGCGCAUCGAGGUGCUGGACAACACCCAGCAGCUGAAGAUCCUGG

CCGACAGCAUCAACAGCGAGAUCGGCAUCCUGUGCAGCGCCCUGCAGAAG

AUCAAGUAA
```

In some embodiments, a suitable mRNA sequence may encode a homolog or an analog of target protein. For example, a homolog or an analog of target protein may be a modified target protein containing one or more amino acid substitutions, deletions, and/or insertions as compared to a wild-type or naturally-occurring target protein while retaining substantial target protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to the above exemplary sequences. In some embodiments, an mRNA suitable for the present invention encodes a protein substantially identical to target protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to the above exemplary sequences. In some embodiments, an mRNA suitable for the present invention encodes a fragment or a portion of target protein. In some embodiments, an mRNA suitable for the present invention encodes a fragment or a portion of target protein, wherein the fragment or portion of the protein still maintains target activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to the above exemplary sequences.

In some embodiments, a suitable mRNA encodes a fusion protein comprising a full length, fragment or portion of a target protein fused to another protein (e.g., an N or C terminal fusion). In some embodiments, the protein fused to the mRNA encoding a full length, fragment or portion of a target protein encodes a signal or a cellular targeting sequence.

Lipid Nanoparticles

According to the present invention, mRNA may be encapsulated or complexed in nanoparticles. In some embodiments, nanoparticles are also referred to as "delivery vehicle," "transfer vehicle", or grammatical equivalents.

According to various embodiments, suitable nanaoparticles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic, non-cationic lipid(s), cholesterol-based lipid(s) and/or PEG-modified lipid(s).

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least 1%, at least 2%, at least 3%, at least 4%, at least 5%, at least 6%, at least 7%, at least 8%, at least 9%, or at least 10% of the total lipids in the liposome.

Cationic Lipids

As used herein, the phrase "cationic lipids" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference. In certain embodiments, cationic lipids suitable for the compositions and methods of the invention include an ionizable cationic lipid described in U.S. provisional patent application 61/617,468, filed Mar. 29, 2012 (incorporated herein by reference), such as, e.g, (15Z, 18Z)—N,N-dimethyl-6-(9Z, 12Z)-octadeca-9, 12-dien-1-yl)tetracosa-15,18-dien-1-amine (HGT5000), (15Z, 18Z)—N,N-dimethyl-6-((9Z, 12Z)-octadeca-9, 12-dien-1-yl)tetracosa-4,15,18-trien-1-amine (HGT5001), and (15Z,18Z)—N,N-dimethyl-6-((9Z, 12Z)-octadeca-9, 12-dien-1-yl)tetracosa-5, 15, 18-trien-1-amine (HGT5002).

In some embodiments, cationic lipids suitable for the compositions and methods of the invention include cationic lipids such as such as 3,6-bis(4-(bis((9Z,12Z)-2-hydroxyoctadeca-9,12-dien-1-yl)amino)butyl)piperazine-2,5-dione (OF-02).

In some embodiments, cationic lipids suitable for the compositions and methods of the invention include a cationic lipid described in WO 2015/184256 A2 entitled "Biodegradable lipids for delivery of nucleic acids" which is incorporated by reference herein such as 3-(4-(bis(2-hydroxydodecyl)amino)butyl)-6-(4-((2-hydroxydodecyl)(2- hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24).

In some embodiments, cationic lipids suitable for the compositions and methods of the invention include a cationic lipid described in WO 2013/063468 and in U.S. provisional application entitled "Lipid Formulations for Delivery of Messenger RNA", both of which are incorporated by reference herein.

In some embodiments, one or more cationic lipids suitable for the present invention may be N-[1-(2,3-dioleyloxy)propyl]-N,N,N-trimethylammonium chloride or "DOTMA". (Feigner et al. (Proc. Nat'l Acad. Sci. 84, 7413 (1987); U.S. Pat. No. 4,897,355). Other suitable cationic lipids include, for example, 5-carboxyspermylglycinedioctadecyl amide or "DOGS," 2,3-dioleyloxy-N-[2(sperminecarboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin- -DMA", 2,2-dilinoleyl-4-dimethylaminoethyl-[1,3]-dioxolane or "DLin-K-XTC2-DMA", and 2-(2,2-di((9Z, 12Z)-octadeca-9,1 2-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, one or more cationic lipids may be chosen from XTC (2,2-Dilinoleyl-4-dimethylaminoethyl-[1, 3]-dioxolane), MC3 (((6Z,9Z,28Z,31Z)-heptatriaconta-6,9, 28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d] [1,3] dioxol-5-amine)), NC98-5 (4,7,13-tris(3-oxo-3-(undecylamino)propyl)-N1,N16-diundecyl-4,7,10,13-tetraazahexadecane-1,16-diamide), In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 30-50% (e.g., about 30-45%, about 30-40%, about 35-50%, about 35-45%, or about 35-40%) of the total lipids in a suitable lipid solution by weight or by molar.

Cholesterol-Based Lipids

In some embodiments, a suitable lipid solution includes one or more cholesterol-based lipids. For example, suitable cholesterol-based cationic lipids include, for example, DC-Choi (N,N-dimethyl-N-ethyl carboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

Exemplary combinations of cationic lipids, non-cationic lipids, cholesterol-based lipids, and PEG-modified lipids are described in the Examples section. For example, a suitable lipid solution may contain cKK-E12, DOPE, cholesterol, and DMG-PEG2K; C12-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; C12-200, DPPC, cholesterol, and DMG-PEG2K; HGT5000, DPPC, cholesterol, and DMG-PEG2K; or HGT5001, DPPC, cholesterol, and DMG-PEG2K. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

mRNA-Loaded Nanoparticles

Any desired lipids may be mixed at any ratios suitable for encapsulating mRNAs. In some embodiments, a suitable lipid solution contains a mixture of desired lipids including cationic lipids, non-cationic lipids, cholesterol and/or PEGylated lipids.

In some embodiments, a process for encapsulating mRNA in lipid nanoparticles comprises mixing an mRNA solution and a lipid solution, wherein the mRNA solution and/or the lipid solution are heated to a pre-determined temperature greater than ambient temperature prior to mixing to form lipid nanoparticles that encapsulate mRNA (see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety).

In some embodiments, a process for encapsulating mRNA in lipid nanoparticles comprises combining pre-formed lipid nanoparticles with mRNA (see U.S. Provisional Application Ser. No. 62/420,413, filed Nov. 10, 2016 and U.S. Provisional Application Ser. No. 62/580,155, filed Nov. 1, 2017, the disclosures of which are hereby incorporated by reference). In some embodiments, combining pre-formed lipid nanoparticles with mRNA results in lipid nanoparticles that show improved efficacy of intracellular delivery of the mRNA. In some embodiments, combining pre-formed lipid nanoparticles with mRNA results in very high encapsulation efficiencies of mRNA encapsulated in lipid nanoparticles (i.e., in the range of 90-95%). In some embodiments, combining pre-formed lipid nanoparticles with mRNA is achieved with pump systems which maintain the lipid/mRNA (N/P) ratio constant throughout the process and which also afford facile scale-up.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as lipid nanoparticles, including liposomes, can be formulated in combination with one or more additional nucleic acids, carriers, targeting ligands or stabilizing reagents, or in pharmacological compositions where it is mixed with suitable excipients. In some embodiments, the lipid nanoparticles encapsulating mRNA are simultaneously administrated with hyaluronidase. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Although the current invention focuses on subcutaneous delivery, which is a bolus injection into the subcutis (the tissue layer between the skin and the muscle), other suitable routes of administration include, for example, oral, rectal, vaginal, transmucosal, pulmonary including intratracheal or inhaled, or intestinal administration; parenteral delivery, including intradermal, transdermal (topical), intramuscular, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Alternatively or additionally, liposomally encapsulated mRNAs and compositions of the invention may be administered in a local rather than systemic manner.

Provided methods of the present invention contemplate single as well as multiple administrations of a therapeutically effective amount of the therapeutic agents (e.g., mRNA encoding a therapeutic protein) described herein. Therapeutic agents can be administered at regular intervals, depending on the nature, severity and extent of the subject's condition (e.g., OTC deficiency). In some embodiments, a therapeutically effective amount of the therapeutic agent (e.g., mRNA encoding a therapeutic protein) of the present invention may be administered subcutaneously periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously.

In some embodiments, provided liposomes and/or compositions are formulated such that they are suitable for extended-release of the mRNA contained therein. Such extended-release compositions may be conveniently administered to a subject at extended dosing intervals. For example, in some embodiments, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release mRNA over extended periods of time. Preferably, the extended-release means employed are combined with modifications made to the mRNA to enhance stability.

As used herein, the term "therapeutically effective amount" is largely based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating OTC deficiency). For example, a therapeutically effective amount may be an amount sufficient to achieve a desired therapeutic and/or prophylactic effect. Generally, the amount of a therapeutic agent (e.g., mRNA encoding a therapeutic protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg to 500 mg/kg body weight, e.g., from about 0.005 mg/kg to 400 mg/kg body weight, from about 0.005 mg/kg to 300 mg/kg body weight, from about 0.005 mg/kg to 200 mg/kg body weight, from about 0.005 mg/kg to 100 mg/kg body weight, from about 0.005 mg/kg to 90 mg/kg body weight, from about 0.005 mg/kg to 80 mg/kg body weight, from about 0.005 mg/kg to 70 mg/kg body weight, from about 0.005 mg/kg to 60 mg/kg body weight, from about 0.005 mg/kg to 50 mg/kg body weight, from about 0.005 mg/kg to 40 mg/kg body weight, from about 0.005 mg/kg to 30 mg/kg body weight, from about 0.005 mg/kg to 25 mg/kg body weight, from about 0.005 mg/kg to 20 mg/kg body weight, from about 0.005 mg/kg to 15 mg/kg body weight, from about 0.005 mg/kg to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg body weight. In some embodiments, the therapeutically effective dose of 1.0 mg/kg body weight is administered intramuscularly or intravenously.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the provided liposomes and compositions comprising mRNA are delivered subcutaneously and the mRNA is expressed in a cell or tissue type other than the subcutis. In some embodiments, the mRNA encoding a target protein delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to, the liver, kidney, heart, spleen, serum, brain, skeletal muscle, lymph nodes, skin, and/or cerebrospinal fluid.

In some embodiments, administering a provided composition results in increased expression of the mRNA administered, or increased activity level of the mRNA-encoded protein in a biological sample from a subject as compared to a baseline expression or activity level before treatment or administration. In some embodiments, administering a provided composition results in increased expression or activity level of the therapeutic protein encoded by the mRNA of a provided composition in a biological sample from a subject as compared to a baseline expression or activity level before treatment. Typically, the baseline level is measured immediately before treatment. Biological samples include, for example, whole blood, serum, plasma, urine and tissue samples (e.g., muscle, liver, skin fibroblasts). In some embodiments, administering a provided composition results in increased therapeutic protein (protein encoded by administered mRNA) expression or activity level by at least about 10%, 20%, 30%, 40%, 50%, 60%, 70%, 80%, 90%, or 95% as compared to the baseline level immediately before treatment. In some embodiments, administering a provided composition results in increased mRNA expression or activity level in a biological sample from a subject as compared to subjects who were not treated. In some embodiments, administering a provided composition results in increased expression or activity level of the therapeutic protein encoded by the mRNA of a provided composition in a biological sample from a subject as compared to subjects who were not treated.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in increased citrulline production in a subject as compared to baseline citrulline production before treatment. Typically, the citrulline level before or after the treatment may be measured in a biological sample obtained from the subject such as blood, plasma or serum, urine, or solid tissue extracts. In some embodiments, treatment according to the present invention results in an increase of the citrulline level in a biological sample (e.g., plasma, serum, or urine) by at least 10%, 20%, 30%, 40%, 50%, 60%, 70%, 80%, 90%, 1-fold, 1.5-fold, 2-fold, 2.5-fold, or 3-fold as compared to the base line citrulline level.

According to the present invention, a therapeutically effective dose of the provided composition, when administered regularly, results in at least one symptom or feature of a protein deficiency being reduced in intensity, severity, or frequency or having delayed onset.

Therapeutic Application

The present invention may be used to treat various diseases, disorders and conditions. In some embodiments, the present invention is useful in treating a liver disease, for example OTC deficiency. Co-injection of mRNA encoding an OTC protein with a hyaluronidase enzyme results in an increased level of OTC enzyme (protein) in a liver cell (e.g., a hepatocyte) of a subject as compared to a baseline level before treatment. Typically, the baseline level is measured before treatment (e.g., up to 12 months prior to the treatment an d in some instances, immediately before the treatment). In some embodiments, suncutaneous injection according to the present invention results in an increased OTC protein level in the liver cell by at least about 10%, 20%, 30%, 40%, 50%, 60%, 70%, 80%, 90%, or 95% as compared to a baseline level before treatment. In some embodiments, suncutaneous injection according to the present invention results in an increased OTC protein level in a liver cell as compared to the OTC protein level a liver cell of subjects who are not treated.

In some embodiments, subcutaneous injection according to the present invention results in an increased OTC protein level in plasma or serum of subject as compared to a baseline level before treatment. Typically, the baseline level is measured before treatment (e.g., up to 12 months prior to the treatment and in some instances, immediately before the treatment). In some embodiments, administering the provided composition results in an increased OTC protein level in plasma or serum by at least about 10%, 20%, 30%, 40%, 50%, 60%, 70%, 80%, 90%, or 95% as compared to a baseline level before treatment. In some embodiments, administering the provided composition results in an increased OTC protein level in plasma or serum as compared to an OTC protein level in plasma or serum of subjects who are not treated.

The compositions and methods of the invention provide for the delivery of mRNA to treat a number of disorders. In particular, the compositions and methods of the present invention are suitable for the treatment of diseases or disorders relating to the deficiency of proteins and/or enzymes that are excreted or secreted in the liver. These include but are not limited to: Phenylalanine hydroxylase (PAH) deficiency (classically known as phenylketonuria, PKU), argininosuccinate synthase 1 (ASS1) deficiency, which causes a liver urea cycle disorder citrullinaemia, erythropoietin (EPO) deficiency, which leads to anemia, erythropoietin being a protein produced both in the kidney and in the liver.

Disorders for which the present invention are useful include, but are not limited to, disorders such as Fabry disease; hemophilic diseases (such as, e.g., hemophilia B (FIX), hemophilia A (FVIII); SMN1-related spinal muscular atrophy (SMA); amyotrophic lateral sclerosis (ALS); GALT-related galactosemia; COL4A5-related disorders including Alport syndrome; galactocerebrosidase deficiencies; X-linked adrenoleukodystrophy; Friedreich's ataxia; Pelizaeus-Merzbacher disease; TSC1 and TSC2-related tuberous sclerosis; Sanfilippo B syndrome (MPS IIIB); the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease.

In some embodiments, the nucleic acids, and in particular mRNA, of the invention may encode functional proteins or enzymes that are secreted into extracellular space. For example, the secreted proteins include clotting factors, components of the complement pathway, cytokines, chemokines, chemoattractants, protein hormones (e.g. EGF, PDF), protein components of serum, antibodies, secretabie toll-like receptors, and others. In some embodiments, the compositions of the present invention may include mRNA encoding erythropoietin, α1-antitrypsin, carboxypeptidase N or human growth hormone.

EXAMPLES

While certain compounds, compositions and methods of the present invention have been described with specificity in accordance with certain embodiments, the following examples serve only to illustrate the compounds of the invention and are not intended to limit the same.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate various nucleic acid materials. Cationic lipids for the process can include, but are not limited to, cKK-E12 (3,6-bis (4-(bis(2-hydroxydodecyl)amino)butyl)piperazine-2,5-dione), OF-02, Target 23, Target 24, ICE, HGT5000, HGT5001, HGT4003, DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), dialkylamino-based, imidazole-based, guanidinium-based, etc.

Helper lipids can include, but are not limited to, DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), DOPC (1,2-dioleyl-sn-glycero-3-phosphotidylcholine), cholesterol, etc. PEGylated lipids can include, but are not limited to, a poly(ethylene) glycol chain of up to 5 kDa in length covalently attached to a lipid with alkyl chain(s) of $C_6$-$C_{20}$ length.

mRNA Materials

In some embodiments, codon-optimized messenger RNA encoding target protein was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A). 5' and 3' untranslated regions present in each mRNA product are represented as X and Y, respectively and defined as stated previously.

Example 1. In Vivo Activity of Expressed hOTC in Mice

This example shows a comparison of intravenous administration without hyaluronidase and subcutaneous administration with and without hyaluronidase at specified respective dosing levels in OTC KO spf$^{ash}$ mice using human OTC (hOTC) mRNA-loaded lipid nanoparticles. FIG. 1 depicts exemplary activity of expressed hOTC protein (in terms of citrulline production) in livers of OTC KO spf$^{ash}$ mice 24 hours after a single dose of hOTC mRNA under different conditions.

The hOTC protein was shown to be enzymatically active, as determined by measuring levels of citrulline production using a custom ex vivo activity assay. Generally, the production of citrulline can be used to evaluate the activity of the expressed hOTC protein. As shown in FIG. 1, exemplary citrulline activity of hOTC protein in the livers of mice was measured 24 hours after the single dose of the lipid nanoparticles encapsulating hOTC mRNA at 20 mg/kg delivered subcutaneously with and without hyaluronidase, respectively. In addition, as a comparison, citrulline activity in the livers of mice was measured 24 hours after a hOTC mRNA lipid nanoparticle solution was injected intravenously at 0.50 mg/kg. Citrulline activity in the livers of saline-treated OTC KO mice was also measured.

As shown in FIG. 1, no significant hOTC protein activity was observed after subcutaneous administration of hOTC mRNA without hyaluronidase co-formulation. hOTC protein activity in those animals was similar to those seen in animals treated with saline. In contrast, hOTC protein activity (as evidenced by citrulline protein levels) was similar in the livers of mice administered the hOTC mRNA LNP composition intravenously and those administered the hOTC mRNA LNP composition formulated with hyluronidase subcutaneously.

Example 2. In Vivo Efficiency of CO-hOTC mRNA Delivery in Mice

This example shows a comparison of intravenous administration without hyaluronidase versus subcutaneous administration with and without hyaluronidase at specified respective dosing levels in OTC KO spf$^{ash}$ mice using CO-hOTC (codon-optimized human OTC) mRNA-loaded lipid nanoparticles. This example illustrates that subcutaneously delivered CO-hOTC mRNA lipid nanoparticles co-formulated with hyaluronidase were more effective than subcutaneously delivered mRNA lipid nanoparticles without hyaluronidase.

Figure 2:
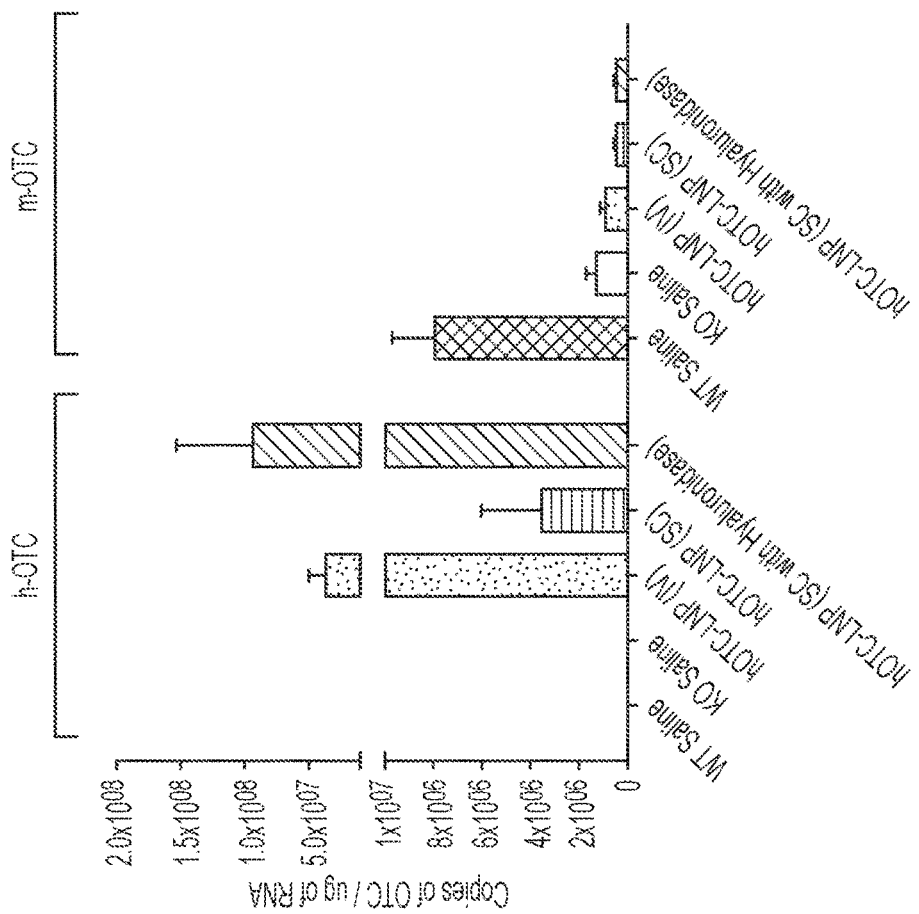
FIG. 2 depicts an exemplary comparison of copy number of codon-optimized human ornithine transcarbamylase (CO-hOTC) mRNA in the livers of OTC KO spf$^{ash}$ mice 24 hours after either intravenous administration or a single subcutaneous administration of an LNP mRNA formulation with and without hyaluronidase.

FIG. 2 depicts exemplary efficiency of delivered CO-hOTC mRNA encapsulated nanoparticles (in terms of CO-hOTC mRNA copy number) in livers of OTC KO spf$^{ash}$ mice 24 hours after a single dose of CO-hOTC mRNA under different conditions.

Efficiency of administration was determined by comparing CO-hOTC mRNA copy number in the livers of the various treatment groups. As shown in FIG. 2, CO-hOTC mRNA copy number in the livers of mice was measured 24 hours after a single 20 mg/kg subcutaneous dose of the CO-hOTC mRNA LNP formulation with and without hyaluronidase. As a comparison, CO-hOTC mRNA copy number was also measured in livers of mice 24 hours after a CO-hOTC mRNA LNP solution was injected intravenously at 0.50 mg/kg. As a control, mOTC mRNA copy number was also measured in the livers of saline-treated wild type (WT) mice, saline-treated OTC KO mice, and OTC KO mice treated intravenously with hOTC LNP solution, subcutaneously with hOTC LNP formulation free of hyaluronidase or subcutaneously with hOTC LNP co-formulated with hyaluronidase.

The results shown in FIG. 2 indicate that a minimal increase was observed in CO-hOTC mRNA copy number in the liver as compared to saline-treated livers after subcutaneous administration without hyaluronidase co-formulation. On the contrary, equivalent levels of CO-hOTC mRNA copies were detected in livers of mice treated with CO-hOTC mRNA LNPs co-formulated with hyaluronidase as compared to intravenous administration. Specifically, 24 hours after subcutaneous dosing of CO-hOTC LNPs co-formulated with hyaluronidase resulted in at least 12-fold endogenous levels.

Example 3. In Vivo Activity of the Expressed hOTC in Mice after mRNA LNP Administration with Hyaluronidase This example shows a comparison of intravenous administration with hyaluronidase versus subcutaneous administration with hyaluronidase at specified respective dosing levels in OTC KO spf$^{ash}$ mice using human OTC (hOTC) mRNA-loaded lipid nanoparticles.

Figure 3:
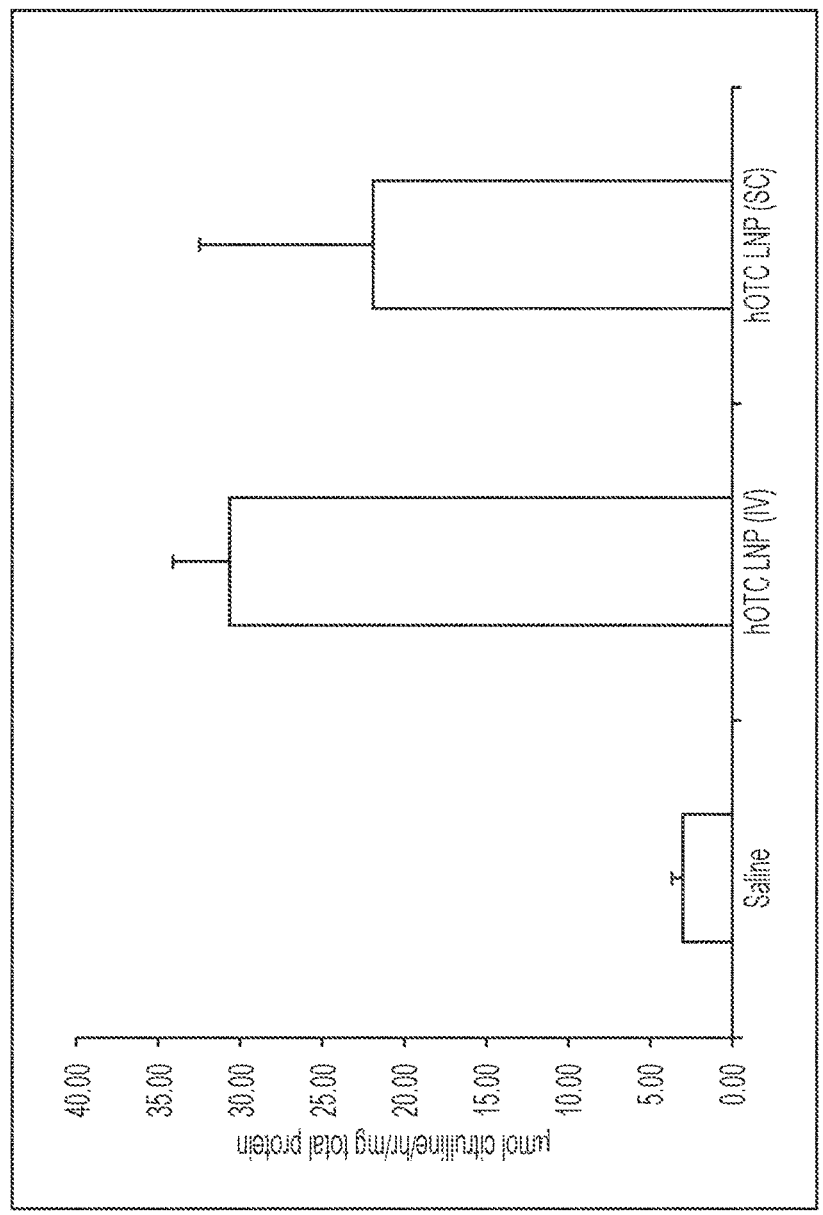
FIG. 3 depicts exemplary citrulline production in the livers of OTC KO spf$^{ash}$ mice 24 hours after either intravenous administration of an LNP mRNA formulation with hyaluronidase or subcutaneous administration of an LNP mRNA formulation with hyaluronidase.

FIG. 3 depicts exemplary activity of expressed hOTC protein (in terms of citrulline production) in livers of OTC KO spf$^{ash}$ mice 24 hours after a single dose of hOTC mRNA under different conditions. Exemplary citrulline activity of hOTC protein in the livers of mice was measured 24 hours after a single 20 mg/kg dose of the hOTC mRNA LNPs was delivered subcutaneously with hyaluronidase. As a comparison, citrulline activity in livers of mice was measured 24 hours after a 0.50 mg/kg intravenous injection of a hOTC mRNA lipid nanoparticle solution with co-formulated with hyaluronidase. Citrulline activity in the livers of saline-treated OTC KO spf$^{ash}$ mice was also measured.

The results shown in FIG. 3 indicate that both single doses of intravenously and subcutaneously administered hOTC mRNA LNP formulations with hyaluronidase resulted in increased hOTC protein activity (as measured by citrulline production) compared to saline treated controls.

Example 4. In Vivo Activity of the Expressed OTC in Mice Compared with Wild-Type Mice This example shows a comparison of levels of OTC protein activity in the livers of untreated wild-type mice and OTC KO spf$^{ash}$ mice treated with subcutaneous administration of hOTC mRNA-loaded lipid nanoparticles with hyaluronidase co-formulation.

Figure 4:
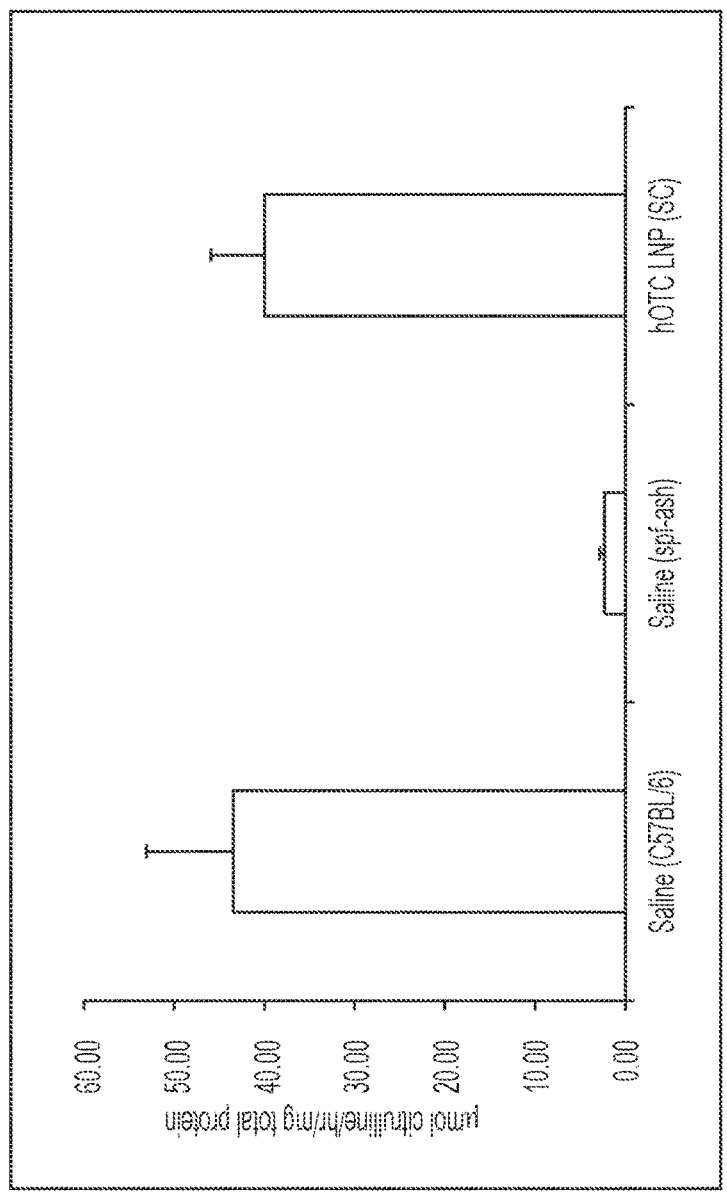
FIG. 4 depicts exemplary citrulline production in the livers of wild-type mice treated with intravenous saline, OTC KO spf$^{ash}$ mice treated with intravenous saline, and KO spf$^{ash}$ mice treated subcutaneously with a CO-hOTC mRNA LNP formulation with hyaluronidase. Citrulline levels were measured 24 hours after administration.

As shown in FIG. 4, exemplary citrulline production as a result of expressed hOTC protein in the livers of mice was measured 24 hours after the single 10 mg/kg dose of CO-hOTC mRNA LNPs delivered subcutaneously, co-formulated with 560 U hyaluronidase. As a comparison, citrulline production in the livers of wild type mice and OTC KO spf$^{ash}$ mice were measured after saline was injected intravenously.

The results shown in FIG. 4 indicate that the levels of citrulline protein measured in the livers of OTC KO mice subcutaneously treated with CO-hOTC co-formulated with hyaluronidase similar to the levels of citrulline protein measured in the livers of saline-treated wild-type mice.

Example 5. Effect of Varying Proportions of Enzyme and mRNA on OTC Expression in Mice Results shown in Table 1 indicate changes in OTC expression levels in mice administered varying proportions of hyaluronidase and mRNA in the composition by subcutaneous delivery. Table 1A shows the dose of mRNA and Hyaluronidase administered to the 11 groups of mice. OTC expression in the respective groups on Day 2 and Day 8 after single administration of the composition is depicted in Table 1B. As shown in Table 1B, OTC expression levels did not significantly alter with increasing doses of hyaluronidase within the range studied. However, good OTC expression level over baseline was observed with 5 mg/Kg mRNA combined with 560 Units of hyaluronidase delivered in 0.3 ml solution. The data also shows that the single dose of the composition effectively results in a sustained protein expression, for at least 8 days.

TABLE 1A

| mRNA concentration in LNP (mg/kg) | Hyaluronidase | | |
|---|---|---|---|
| | 280 U/0.3 mL | 560 U/0.3 mL | 1120 U/0.3 mL |
| 0.5 | GROUP 1 | GROUP 2 | GROUP 3 |
| 1.0 | GROUP 4 | GROUP 5 | GROUP 6 |
| 2.5 | GROUP 7 | GROUP 8 | GROUP 9 |
| 5.0 | | GROUP 10 | |
| 0.0 | | GROUP 11 | |

TABLE 1B

| Group No. | Hylauronidase enzyme | mRNA Dose Level (mg/kg) | μmol/hr/mg of total protein | |
|---|---|---|---|---|
| | | | Day 2 | Day 8 |
| 1 | (WT) | NA | 74.3 ± 12.6 | |
| 2 | (KO) | NA | 3.8 ± 0.4 | |
| 3 | GROUP 1 (280 U/0.3 mL) | 0.5 | 3.2 ± 0.8 | 3.5 ± 0.6 |

TABLE 1B-continued

| Group No. | Hylauronidase enzyme | mRNA Dose Level (mg/kg) | μmol/hr/mg of total protein | |
|---|---|---|---|---|
| | | | Day 2 | Day 8 |
| 4 | GROUP 2 (560 U/0.3 mL) | 0.5 | 4.2 ± 0.6 | 4.1 ± 0.7 |
| 5 | GROUP 3 (1120 U/0.3 mL) | 0.5 | 4.0 ± 0.2 | 3.8 ± 0.5 |
| 6 | GROUP 4 (280 U/0.3 mL) | 1.0 | 6.3 ± 3.3 | 4.6 ± 0.5 |
| 7 | GROUP 5 (560 U/0.3 mL) | 1.0 | 4.5 ± 0.8 | 4.6 ± 0.7 |
| 8 | GROUP 6 (1120 U/0.3 mL) | 1.0 | 4.3 ± 1.3 | 3.7 ± 0.1 |
| 9 | GROUP 7 (280 U/0.3 mL) | 2.5 | 13.8 ± 5.7 | 10.8 ± 4.9 |
| 10 | GROUP 8 (560 U/0.3 mL) | 2.5 | 11.3 ± 6.0 | 3.5 ± 0.5 |
| 11 | GROUP 9 (1120 U/0.3 mL) | 2.5 | 10.1 ± 4.3 | 4.3 ± 1.5 |
| 12 | GROUP 10 (560 U/0.3 mL) | 5.0 | 26.3 ± 10.3 | 22.6 ± 9.3 |
| 13 | GROUP 11 (560 U/0.3 mL) | 0 | 4.5 ± 0.3 | 3.3 ± 0.4 |

Figure 5:
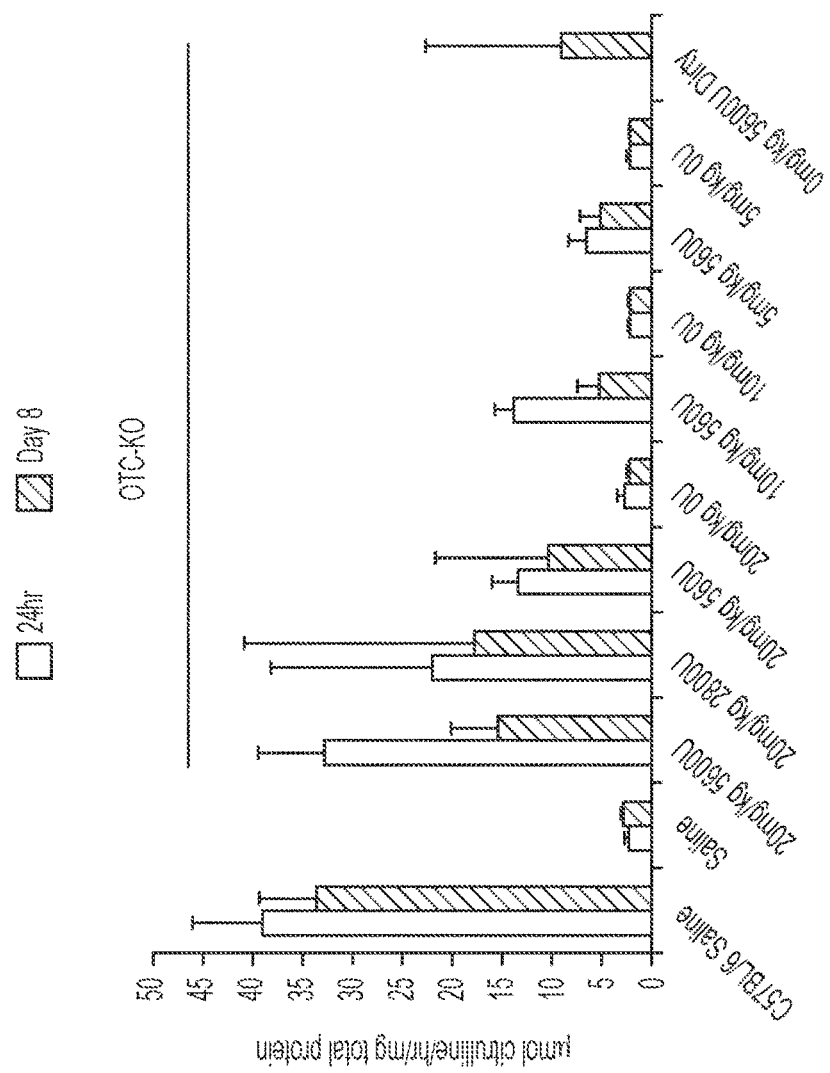
FIG. 5 depicts exemplary OTC activity as an effect of varying hyaluronidase dose in the composition. OTC-KO mice were treated with 5, 10 or 20 mg/Kg OTC mRNA and 0, 560 U, 2800 U or 5600 U of hyaluronidase as shown in the figure and citrulline level was measured.

In contrast, at higher dose of mRNA (20 mg/Kg), shown in FIG. 5, a distinct effect of hyaluronidase dose was observed in resultant OTC activity in the OTC knock-out mice, as measured by citrulline assay. At 24 hours post-administration, 5600 U of hyaluronidase induced double the OTC activity measured by citrulline, compared to 560 U of hyaluronidase (FIG. 5). Strikingly, as was also shown previously, citrulline was nearly undetectable when hyaluronidase was not administered in the composition.

Example 6. In Vivo Activity of the Expressed PAH in Mice

This example shows a comparison of intravenous administration without hyaluronidase versus subcutaneous administration with hyaluronidase in phenylalanine hydroxylase (PAH) KO mice (mouse model for phenylketonuria (PKU)) using CO-hPAH (codon-optimized human PAH) mRNA-loaded lipid nanoparticles.

Figure 6:
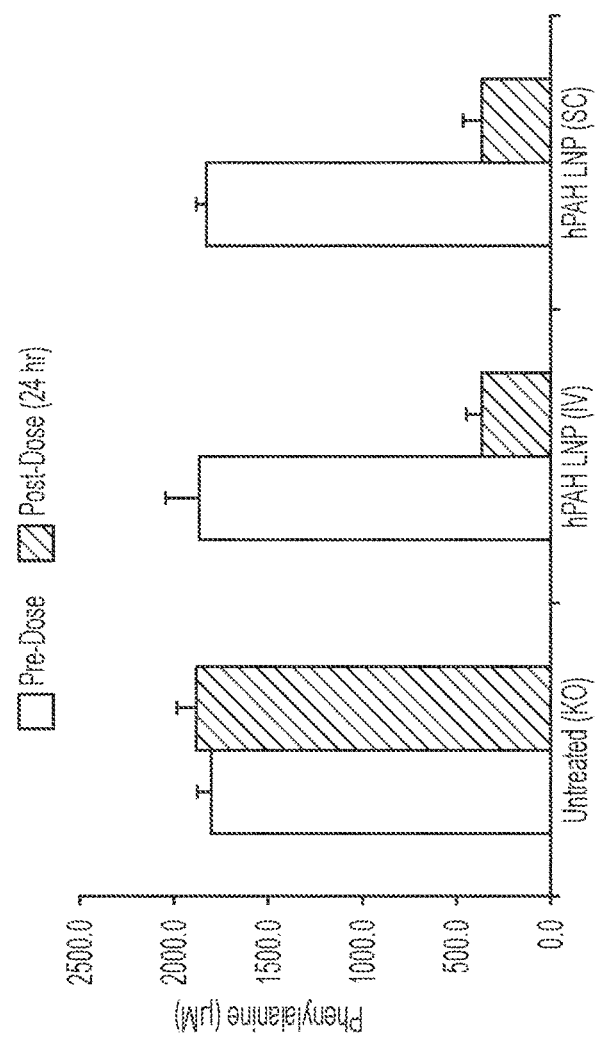
FIG. 6 depicts exemplary serum phenylalaine levels (pre- and post-administration) in PAH KO mice 24 hours after either subcutaneous administration of a codon optimized hPAH (CO-hPAH) LNP mRNA formulation with hyaluronidase or intravenous administration of a CO-hPAH LNP mRNA formulation.

FIG. 6 depicts exemplary serum phenylalanine levels in PAH KO mice 24 hours after a single dose of hOTC mRNA lipid nanoparticles under different conditions.

As shown in FIG. 6, exemplary serum phenylalanine levels in PAH KO mice were measured before and 24 hours after a single 20 mg/kg subcutaneous dose of CO-hPAH mRNA LNPs co-formulated with 5600 U hyaluronidase. Serum phenylalanine levels in PAH KO mice were also measured before and 24 hours after intravenous injection of 1.0 mg/kg CO-hPAH mRNA LNP solution. Serum phenylalanine levels in untreated PAH KO mice were also measured. The results shown in FIG. 6 indicate equivalent normalization of the clinically relevant phenylalanine biomarker was achieved via both routes of administration.

Example 7. In Vivo Expression of ASS1 in Mice

This example shows a comparison of intravenous administration without hyaluronidase versus subcutaneous administration with hyaluronidase in argininosuccinate synthetase (ASS1) KO mice (mouse model citrullenemia) using CO-hASS1 (codon-optimized human ASS1) mRNA-loaded lipid nanoparticles.

Figure 7:
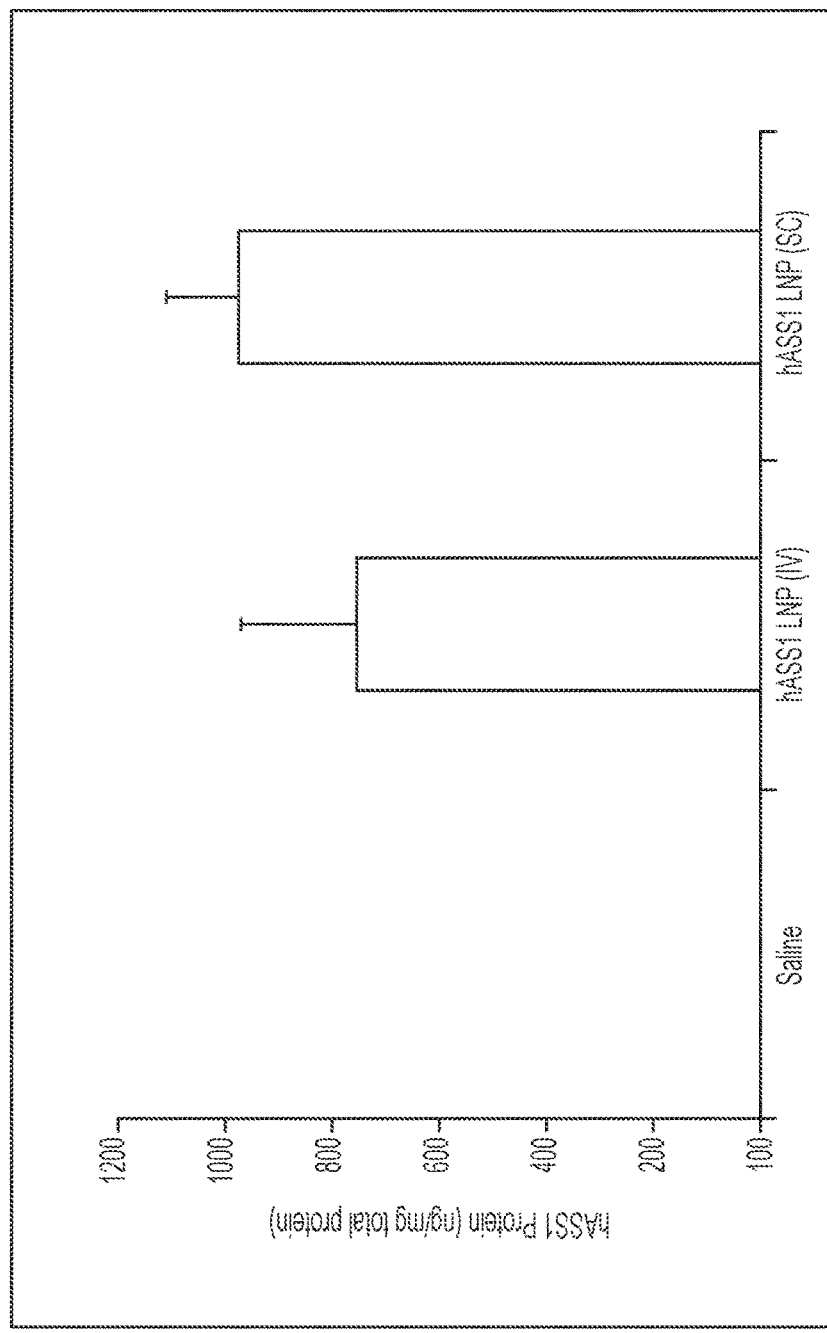
FIG. 7 depicts exemplary human argininosuccinate synthetase (hASS1) protein levels in livers of ASS1 KO mice 24 hours after either subcutaneous administration of a codon optimized hASS1 (CO-hASS1) mRNA LNP formulation with hyaluronidase or intravenous administration of a CO-hASS1 mRNA LNP formulation.

FIG. 7 depicts exemplary levels of hASS1 protein in the livers of ASS1 KO mice 24 hours after a single dose of hASS1 mRNA lipid nanoparticles under different conditions.

As shown in FIG. 7, exemplary hASS1 protein levels in the livers of ASS1 KO mice were measured 24 hours after a single 20 mg/kg subcutaneous dose of CO-hASS1 mRNA LNPs co-formulated with 5600 U hyaluronidase. Liver ASS1 protein levels in ASS1 KO mice were also measured 24 hours after intravenous injection of 1.0 mg/kg CO-hASS1 mRNA LNP solution. Liver ASS1 protein levels in saline-treated ASS1 KO mice were also measured. The results shown in FIG. 7 indicate that significant levels of hASS1 protein were observed in the livers of mice treated with both routes of administration.

Example 8. In Vivo Expression of Firefly Luciferase Protein in Mice

This example illustrates exemplary methods of administering firefly luciferase (FFL) mRNA-loaded LNPs and methods for analyzing firefly luciferase in target tissues in vivo.

Figure 8:
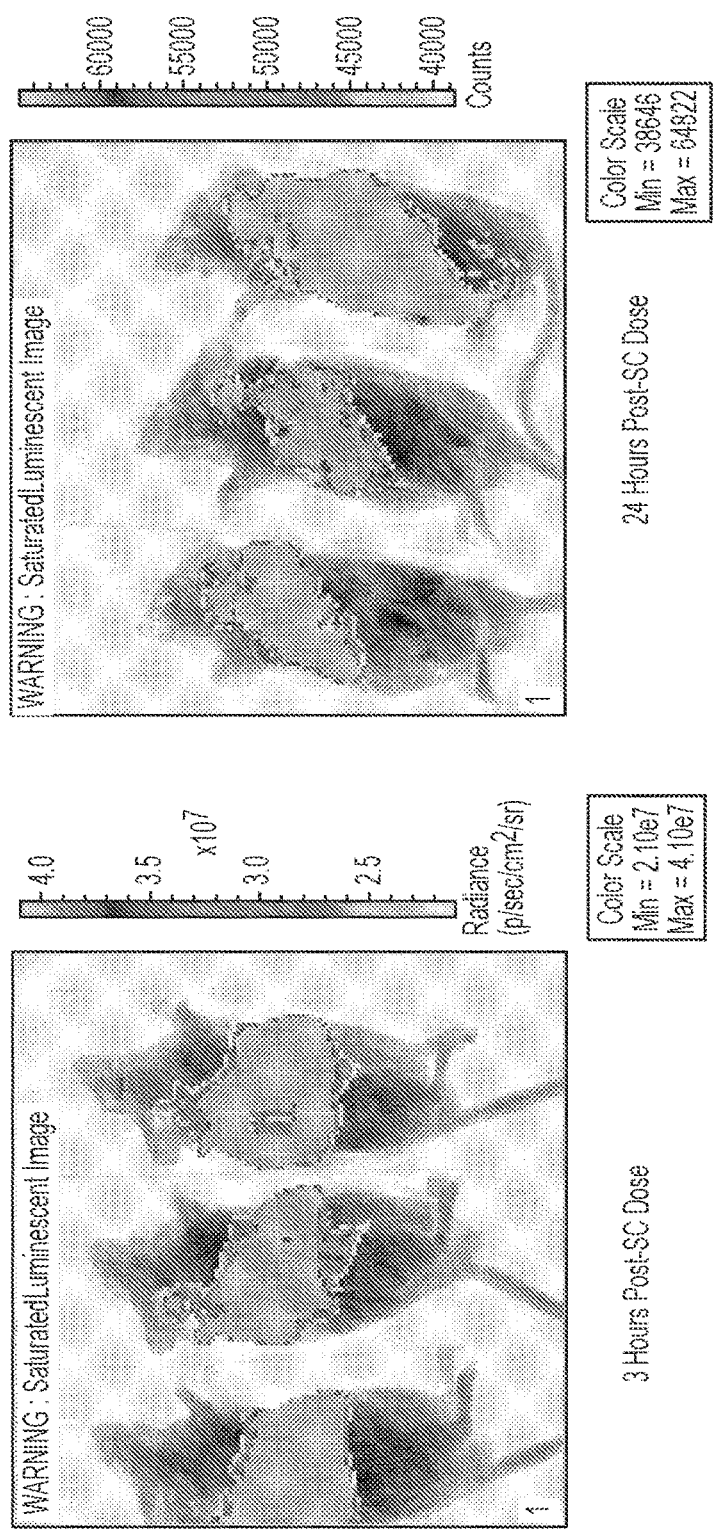
FIG. 8 depicts an exemplary measurement of Firefly Luciferase (FFL) protein activity assessed via luminescence output using a whole body in vivo luminometer. FFL protein luminescence was observed in wide type mice liver 3 hours and 24 hours after a subcutaneous administration of FFL mRNA LNP formulation with hyaluronidase. Luminescence intensity was maintained throughout this period.

Wild type mice were treated with LNPs encapsulating mRNA encoding FFL at 20 mg/kg co-formulated with hyaluronidase (5600 U) by subcutaneous delivery. In FIG. 8, the graph on the left depicts luminescence produced by FFL protein observed at 3 hours post-subcutaneous administration. The graph on the right depicts luminescence produced by FFL protein observed at 24 hours post-subcutaneous administration.

The results shown in FIG. 8 indicate that lipid nanoparticle mRNA formulation co-injected with hyaluronidase via subcutaneous route resulted in extended target protein activity. Significant luminescence was observed representing the successful production of active FFL protein in the livers of these mice. Further, sustained FFL activity was maintained for at least 24 hours with little to no decrease in intensity.

Example 9. In Vivo Expression of Human Erythropoietin (hEPO) in Mice

This example illustrates an exemplary time course of human erythropoietin (hEPO) protein expression following subcutaneous administration of hEPO encoding mRNA using the method disclosed, in comparison with intravenous administration of the same.

Male CD1 mice were administered either an intravenous dose of hEPO mRNA-loaded lipid nanoparticles at a dosage of 1 mg/kg or a subcutaneous dose of hEPO mRNA-loaded lipid nanoparticles at a dosage of 5 mg/kg co-formulated with 5600 U hyaluronidase once on day 1. Human EPO protein expression was examined in serum samples by hEPO-specific ELISA for 4 days.

Figure 9:
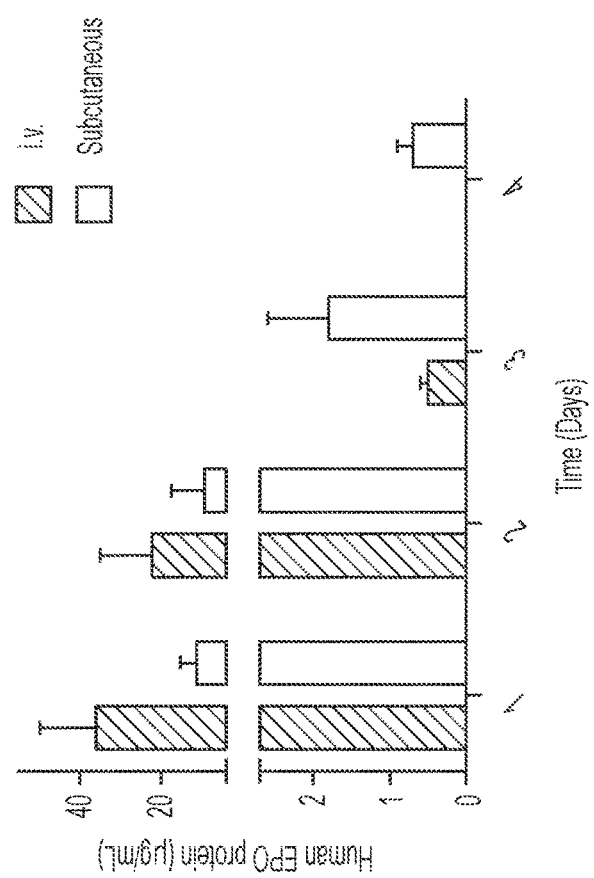
FIG. 9 depicts exemplary human erythropoietin (hEPO) protein levels in serum of mice 1-4 days after either subcutaneous administration of hEPO mRNA LNP formulation with hyaluronidase or intravenous administration of hEPO mRNA LNP formulation.

As shown in FIG. 9, high level of EPO protein expression was observed in both intravenous-administered and subcutaneous-administered groups of mice at 6 hours after mRNA administration (Day 1) and on Day 2. Surprisingly, on Days 3 and 4, serum hEPO expression levels were higher in mice that received subcutaneous injections compared to those that received intravenous injections.

Figure 10:
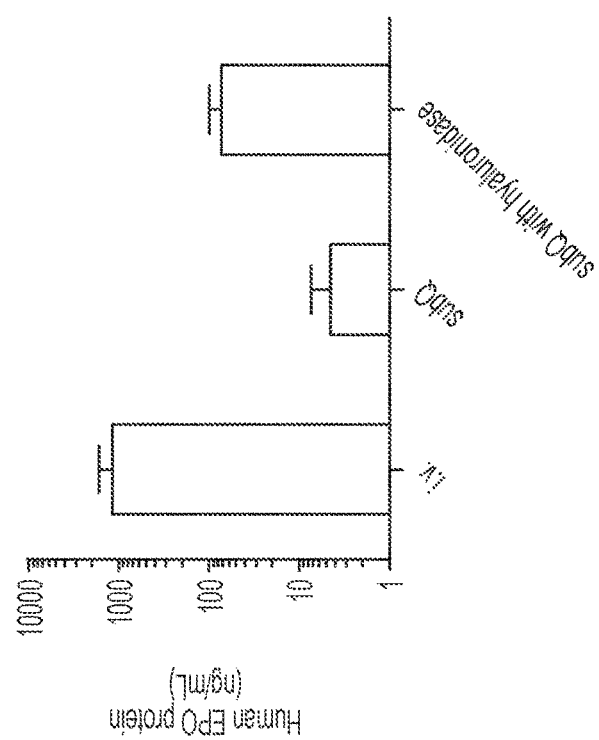
FIG. 10 depicts exemplary human EPO protein expression in mouse serum, after administration of hEPO mRNA subcutaneously with or without hyaluronidase. hEPO expression upon intravenous administration is shown for comparison.

FIG. 10 shows expression of human EPO in mice after administering human EPO encoding mRNA subcutaneously (SubQ) with or without hyaluronidase. As shown for other mRNA, subcutaneous administration of the mRNA LNP in absence of hyaluronidase results in poor expression, whereas with hyaluronidase there is significant increase in the protein in the serum. The expression level is compared to intravenous administration for the same mRNA LNP.

Example 10. Effect of PEGylated Lipid in LNP on Protein Expression

Higher percentage of PEGylated lipid-LNP was shown to induce higher protein expression when mRNA was delivered via the subcutaneous delivery (20 mg/Kg mRNA), as shown in Table 2. Four groups of mice were administered saline or LNP via intravenous or subcutaneous delivery routes. ASS1 expression was dramatically increased when the subcutaneously administered composition comprised 5% PEG-LNP, compared to 3% PEG-LNP. Intravenously administered composition showed opposite effect. Low concentration of PEGylated lipid induced high level of ASS1 expression.

TABLE 2

| Group No. | % PEGylated LNP | Dose Level (mg/kg) | ASS1 (ng ASS1/ mg of protein) |
|---|---|---|---|
| 1 | Saline | 0.0 | — |
| 2 | (i.v.) | 0.5 | 756 ± 215 |
| 2 | (subQ) 3% PEG LNP | 20.0 | 225 ± 134 |
| 3 | (subQ) 5% PEG LNP | 20.0 | 977 ± 228 |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A method of delivering an mRNA to a cell in vivo comprising administering via subcutaneous or intramuscular injection to a subject in need of treatment a) an mRNA encoding a protein, at a concentration of greater than 1 mg/kg, wherein the mRNA is encapsulated in a lipid-based nanoparticle (LNP) and b) a hyaluronidase enzyme, at a concentration of at least 200 U.

2. The method of claim 1, wherein the subcutaneous or intramuscular injection results in delivery of the mRNA in the liver.

3. The method of claim 1, wherein the subcutaneous or intramuscular injection results in expression of the protein in the liver of the subject.

4. The method of claim 1, wherein the subcutaneous or intramuscular injection results in expression of the protein in the serum of the subject.

5. The method of claim 1, wherein the lipid-based nanoparticle is a liposome.

6. The method of claim 5, wherein the liposome comprises a PEGylated lipid.

7. The method of claim 6, wherein the PEGylated lipid constitutes at least 1%, at least 2%, at least 3%, at least 4%, at least 5%, at least 6%, at least 7%, at least 8%, at least 9%, or at least 10% of the total lipids in the liposome.

8. The method of claim 1, wherein the hyaluronidase enzyme is at a concentration of at least 220 U.

9. The method of claim 1, wherein the hyaluronidase enzyme is at a concentration of at least 260 U.

10. A method of treating a disease, disorder or condition comprising delivering messenger RNA (mRNA) to a subject in need of treatment according to a method of claim 1, wherein the mRNA encodes a protein deficient in the subject.

11. A composition for treating ornithine transcarbamylase (OTC deficiency), comprising a) an mRNA encoding an ornithine transcarbamylase (OTC) protein, at a concentration of greater than 1 mg/kg, wherein the mRNA is encapsulated in a lipid-based nanoparticle (LNP) and b) a hyaluronidase enzyme, at a concentration of at least 200 U.

12. The composition of claim 11, wherein the mRNA and/or the hyaluronidase enzyme is encapsulated within a nanoparticle.

13. The composition of claim 11, wherein the mRNA and the hyaluronidase enzyme are encapsulated within the same nanoparticle.

14. The composition of claim 11, wherein the mRNA and the hyaluronidase enzyme are encapsulated within separate nanoparticles.

15. The composition of claim 11, wherein the separate nanoparticles encapsulating the mRNA and the hyaluronidase enzyme comprise the same formulation.

16. The composition of claim 11, wherein the separate nanoparticles encapsulating the mRNA and the hyaluronidase enzyme comprise different formulations.

17. The composition of claim 11, wherein the mRNA is encapsulated within the nanoparticle and the hyaluronidase enzyme is not encapsulated.

* * * * *